US009499628B2

(12) United States Patent
Way

(10) Patent No.: US 9,499,628 B2
(45) Date of Patent: Nov. 22, 2016

(54) METHOD OF BOOSTING THE IMMUNE RESPONSE IN NEONATES

(71) Applicant: CHILDREN'S HOSPITAL MEDICAL CENTER, Cincinnati, OH (US)

(72) Inventor: Sing Sing Way, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 153 days.

(21) Appl. No.: 14/304,803

(22) Filed: Jun. 13, 2014

(65) Prior Publication Data

US 2014/0370004 A1 Dec. 18, 2014

Related U.S. Application Data

(60) Provisional application No. 61/835,427, filed on Jun. 14, 2013.

(51) Int. Cl.
*A61K 39/395* (2006.01)
*C07K 16/28* (2006.01)
*A61K 39/00* (2006.01)

(52) U.S. Cl.
CPC ..... *C07K 16/2881* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 4,444,887 A | 4/1984 | Hoffman | |
| 4,716,111 A | 12/1987 | Osband et al. | |
| 5,225,539 A | 7/1993 | Winter | |
| 5,530,101 A | 6/1996 | Queen et al. | |
| 5,565,332 A | 10/1996 | Hoogenbom et al. | |
| 5,585,089 A | 12/1996 | Queen et al. | |
| 5,667,781 A * | 9/1997 | Trowbridge | C07K 16/2881 424/143.1 |

FOREIGN PATENT DOCUMENTS

| | | | |
|---|---|---|---|
| EP | 0 519 596 A1 | 12/1992 | |
| EP | 0 592 106 A1 | 4/1994 | |
| EP | 0 239 400 B1 | 8/1994 | |
| FR | WO 2005111082 A1 * | 11/2005 | C07K 16/2881 |
| WO | WO 91/09967 | 7/1991 | |
| WO | WO 91/10741 | 7/1991 | |
| WO | WO 96/33735 | 10/1996 | |
| WO | WO 96/34096 | 10/1996 | |
| WO | WO 98/16654 | 4/1998 | |
| WO | WO 98/24893 | 6/1998 | |
| WO | WO 98/46645 | 10/1998 | |
| WO | WO 98/50433 | 11/1998 | |

OTHER PUBLICATIONS

Shimoyama et al., The third nation-wide study on adult T-cell leukemia/lymphoma (ATL) in Japan: characteristic patterns of HLA antigen and HTLV-I infection in ATL patients and their relatives. The T- and B-cell Malignancy Study Group, Int J Cancer. Apr. 15, 1988; 41(4):505-12.*
Rabinovich et al., Immunosuppressive strategies that are mediated by tumor cells, Annu Rev Immunol. 2007;25:267-96.*
Kemp et al., J Immunol 1987; 138:2422-2426.*
Bjorn et al., Cancer Res. Dec. 15, 1987;47(24 Pt 1):6639-45.*
Adkins, B., Bu, Y., Cepero, E. & Perez, R. Exclusive Th2 primary effector function in spleens but mixed Th1/Th2 function in lymph nodes of murine neonates. J Immunol 164, 2347-2353 (2000).
Adkins, B., Leclerc, C. & Marshall-Clarke, S. Neonatal adaptive immunity comes of age. Nature reviews. Immunology 4, 553-564, (2004).
Aluvihare, V. R., Kallikourdis, M. & Betz, A. G. Regulatory T cells mediate maternal tolerance to the fetus. Nature Immunology 5, 266-271, (2004).
Andrassy, J. et al., "Tolerance to Noninherited Maternal MHC Antigens in Mice," The Journal of Immunology, vol. 171, pp. 5554-5561 (2003).
Brombacher, F. et al. IL-12 is dispensable for innate and adaptive immunity against low doses of Listeria monocytogenes. International Immunology 11, 325-332 (1999).
Burlingham, W. J. & Benichou, G. Bidirectional alloreactivity: A proposed microchimerism-based solution to the NIMA paradox. Chimerism 3, 29-36, (2012).
Dong, H. Y., Wilkes, S. & Yang, H. CD71 is selectively and ubiquitously expressed at high levels in erythroid precursors of all maturation stages: a comparative immunochemical study with glycophorin A and hemoglobin A. The American Journal of Surgical Pathology 35, 723-732, (2011).
Forsthuber, T., Yip, H. C. & Lehmann, P. V. Induction of TH1 and TH2 immunity in neonatal mice. Science 271, 1728-1730 (1996).
Fuchs, E. J., Ridge, J. P. & Matzinger, P. Response: immunological tolerance. Science 272, 1406-1408, (1996).
Gellin, B. G. & Broome, C. V. Listeriosis. JAMA 261, 1313-1320 (1989).
Harty, J. T. & Bevan, M. J. Specific immunity to Listeria monocytogenes in the absence of IFN gamma. Immunity 3, 109-117 (1995).
Havell, E. A. Evidence that tumor necrosis factor has an important role in antibacterial resistance. J Immunol 143, 2894-2899 (1989).
Hermansen, M. C. Nucleated red blood cells in the fetus and newborn. Archives of disease in childhood. Fetal and neonatal edition 84, F211-215 (2001).
Kollmann, T. R. et al. Neonatal innate TLR-mediated responses are distinct from those of adults. J Immunol 183, 7150-7160, (2009).

(Continued)

*Primary Examiner* — Michael Szperka
(74) *Attorney, Agent, or Firm* — Knobbe, Martens, Olson & Bear, LLP

(57) ABSTRACT

In an aspect, a method of augmenting an immune response in a subject in need thereof, comprising identifying the subject, and treating the subject to inhibit the immune suppressive effect of $CD71^+$ cells is provided. Further provided is a method of preventing, treating or ameliorating an infection in a subject, comprising administering to the subject an agent that reduces the level of $CD71^+$ cells in the subject.

10 Claims, 21 Drawing Sheets

(56) References Cited

OTHER PUBLICATIONS

Kollmann, T. R., Levy, O., Montgomery, R. R. & Goriely, S. Innate immune function by Toll-like receptors: distinct responses in newborns and the elderly. Immunity 37, 771-783, (2012).
Lee, H. H. et al. Delayed maturation of an IL-12-producing dendritic cell subset explains the early Th2 bias in neonatal immunity. The Journal of Experimental Medicine 205, 2269-2280, (2008).
Leikin, S. L. et al. Mortality in children and adolescents with sickle cell disease. Cooperative Study of Sickle Cell Disease. Pediatrics 84, 500-508 (1989).
Levy, O. et al. Selective impairment of TLR-mediated innate immunity in human newborns: neonatal blood plasma reduces monocyte TNF-alpha induction by bacterial lipopeptides, lipopolysaccharide, and imiquimod, but preserves the response to R-848. J Immunol 173, 4627-4634 (2004).
Marsee, D. K., Pinkus, G. S. & Yu, H. CD71 (transferrin receptor): an effective marker for erythroid precursors in bone marrow biopsy specimens. American Journal of Clinical Pathology 134, 429-435, (2010).
Mold, J. E. & McCune, J. M. Immunological tolerance during fetal development: from mouse to man. Advances in Immunology 115, 73-111, (2012).
Mold, J. E. et al. Maternal alloantigens promote the development of tolerogenic fetal regulatory T cells in utero. Science 322, 1562-1565, (2008).
Padlan, E. A., A possible procedure for reducing the immunogenicity of antibody variable domains while preserving their ligand-binding properties, *Molecular Immunology* 28(4/5):489-498 (1991).
Pasparakis, M., Alexopoulou, L., Episkopou, V. & Kollias, G. Immune and inflammatory responses in TNF alpha-deficient mice: a critical requirement for TNF alpha in the formation of primary B cell follicles, follicular dendritic cell networks and germinal centers, and in the maturation of the humoral immune response. The Journal of Experimental Medicine 184, 1397-1411 (1996).
PrabhuDas, M. et al. Challenges in infant immunity: implications for responses to infection and vaccines. Nature immunology 12, 189-194, (2011).
Ridge, J. P., Fuchs, E. J. & Matzinger, P. Neonatal tolerance revisited: turning on newborn T cells with dendritic cells. Science 271, 1723-1726 (1996).
Roguska et al., Humanization of murine monoclonal antibodies through variable domain resurfacing, PNAS 91:969-973 (1994).
Rowe, J. H., Ertelt, J. M., Aguilera, M. N., Farrar, M. A. & Way, S. S. Foxp3(+) regulatory T cell expansion required for sustaining pregnancy compromises host defense against prenatal bacterial pathogens. Cell Host & Microbe 10, 54-64, (2011).
Rowe, J. H., Ertelt, J. M., Xin, L. & Way, S. S., Pregnancy imprints regulatory memory that sustains anergy to fetal antigen. Nature 490, 102-106, (2012).
Samstein, R. M., Josefowicz, S. Z., Arvey, A., Treuting, P. M. & Rudensky, A. Y. Extrathymic generation of regulatory T cells in placental mammals mitigates maternal-fetal conflict. Cell 150, 29-38, (2012).
Siegrist, C.A., Neonatal and early life vaccinology, Vaccine 19, 3331-3346 (2001).
Studnicka et al., Human-engineered monoclonal antibodies retain full specific binding activity by preserving non-CDR complementarity-modulating residues, Protein Engineering 7(6):805-814 (1994).
Trowbridge, I. S., Lesley, J. & Schulte, R. Murine cell surface transferrin receptor: studies with an anti-receptor monoclonal antibody. Journal of Cellular Physiology 112, 403-410, (1982).
Zaghouani, H., Hoeman, C. M. & Adkins, B. Neonatal immunity: faulty T-helpers and the shortcomings of dendritic cells. Trends in immunology 30, 585-591, (2009).

* cited by examiner

METHOD OF BOOSTING THE IMMUNE RESPONSE IN NEONATES

STATEMENT REGARDING FEDERALLY SPONSORED R&D

This invention was made with government support under AI087830, and AI100934 awarded by the National Institutes of Health. The government has certain rights in the invention.

INCORPORATION BY REFERENCE TO ANY PRIORITY APPLICATIONS

Any and all priority claims identified in the Application Data Sheet, or any correction thereto, are hereby incorporated by reference under 37 CFR 1.57.

BACKGROUND

Field

This disclosure is directed to infection susceptibility in neonates.

Description of the Related Technology

Newborn infants are highly susceptible to infection. These defects in host defense have been generally ascribed to functional immaturity of immune cells in neonates compared with adults[1-3]. However, the degree of hyporesponsiveness among neonatal cells is highly variable depending on stimulation conditions[4-11]. This discordance suggests a more unifying explanation is needed to explain why immunity is compromised in newborns.

SUMMARY

Some embodiments provide a method of boosting an immune response in neonates and newborns comprising administering to a neonate or newborn in need thereof an anti-CD71 antibody.

Some embodiments provide a method of boosting an immune response in neonates and newborns comprising administering to a neonate or newborn in need thereof an anti-CD71 antibody whereby the immunosuppressive effect of $CD71^+$ cells is inhibited.

Some embodiments provide a method of identifying an immune response stimulating agent, comprising: providing $CD71^+$ cells; providing an agent; and assaying the ability of said agent to suppress the immunosuppressive effect of $CD71^+$ cells.

Some embodiments provide a pharmaceutical composition for reducing an immune response in a subject comprising a $CD71^+$ stimulator and a pharmaceutically acceptable carrier.

Some embodiments provide a method of screening a compound library comprising: (a) obtaining a library comprising a plurality of compound structures; (b) obtaining $CD71^+$ cells; and (c) identifying compounds which inhibit production of TNF-α.

Some embodiments provide a method of ameliorating, preventing or treating an infection in an individual, the method comprising administering to the individual in need thereof an effective amount of a compound identified by the method of screening a compound library as disclosed and described herein.

Some embodiments provide a method of ameliorating, preventing or treating an infection in an individual, the method comprising administering to the individual an effective amount of an agent that down regulates $CD71^+$ cells.

Some embodiments provide a method of ameliorating, preventing or treating an infection in an individual, the method comprising: filtering blood of the individual to separate $CD71^+$ cells from the blood.

Some embodiments provide a method of ameliorating, preventing or treating an infection in an individual, the method comprising administering to the individual an effective amount of an agent whereby the immunosuppressive effect of $CD71^+$ cells is inhibited.

Some embodiments provide a pharmaceutical composition for any one of the methods as disclosed and described herein for boosting an immune response in neonates and newborns comprising a $CD71^+$ inhibitor and a pharmaceutically acceptable carrier.

Some embodiments provide a pharmaceutical composition for boosting an immune response in neonates and newborns comprising a $CD71^+$ inhibitor and a pharmaceutically acceptable carrier.

Some embodiments provide a method of augmenting an immune response in a subject in need thereof, comprising identifying the subject, and treating the subject to inhibit the immune suppressive effect of $CD71^+$ cells.

Some embodiments provide a method of preventing, treating or ameliorating an infection in a subject, comprising administering to the subject an agent that reduces the level of $CD71^+$ cells in the subject.

Some embodiments provide a method of identifying a modifier of an immune response, comprising providing $CD71^+$ cells, providing an agent to the $CD71^+$ cells, and assessing the ability of the agent to modify the immunosuppressive effect of the $CD71^+$ cells.

Some embodiments provide a pharmaceutical composition for modifying an immune response comprising an agent identified by the method as disclosed and described herein and a pharmaceutically acceptable carrier.

BRIEF DESCRIPTION OF THE DRAWINGS

Adoptively Transferred Adult Immune Cells do not Override Neonatal Infection Susceptibility (FIGS. 1A-E)

Figure 2A:
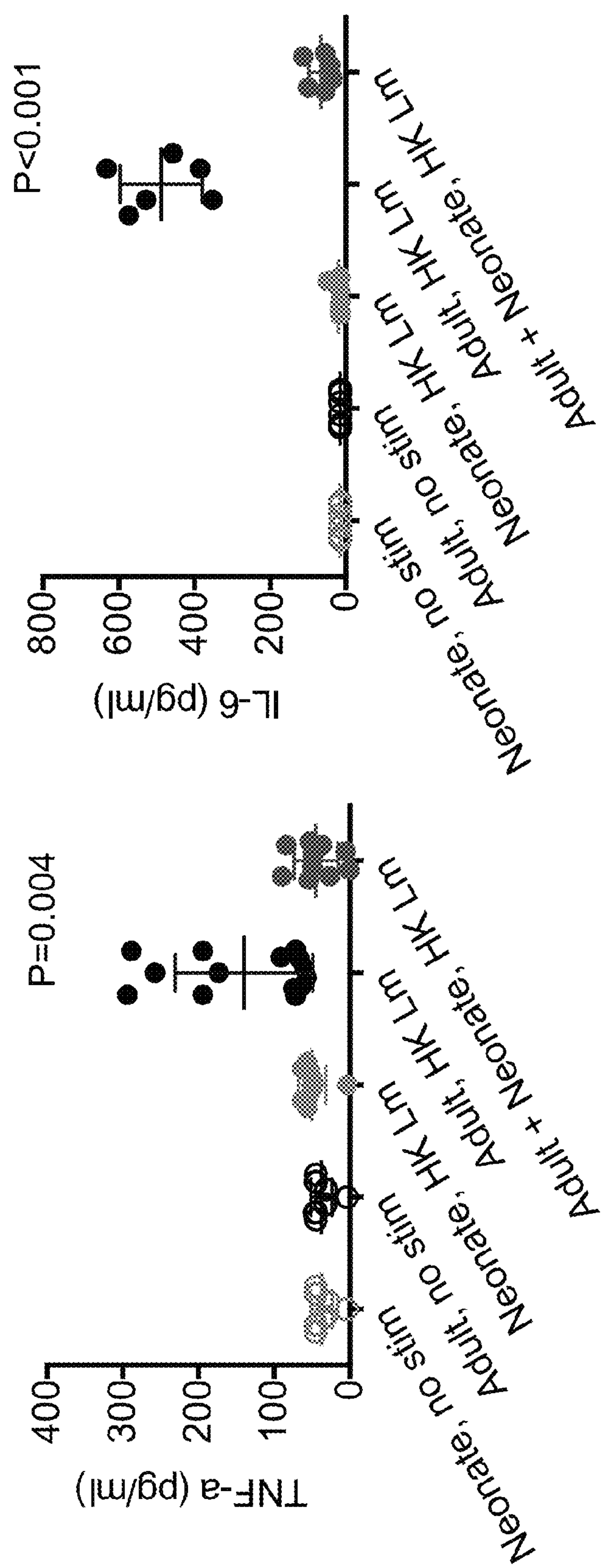
Figure 2B:
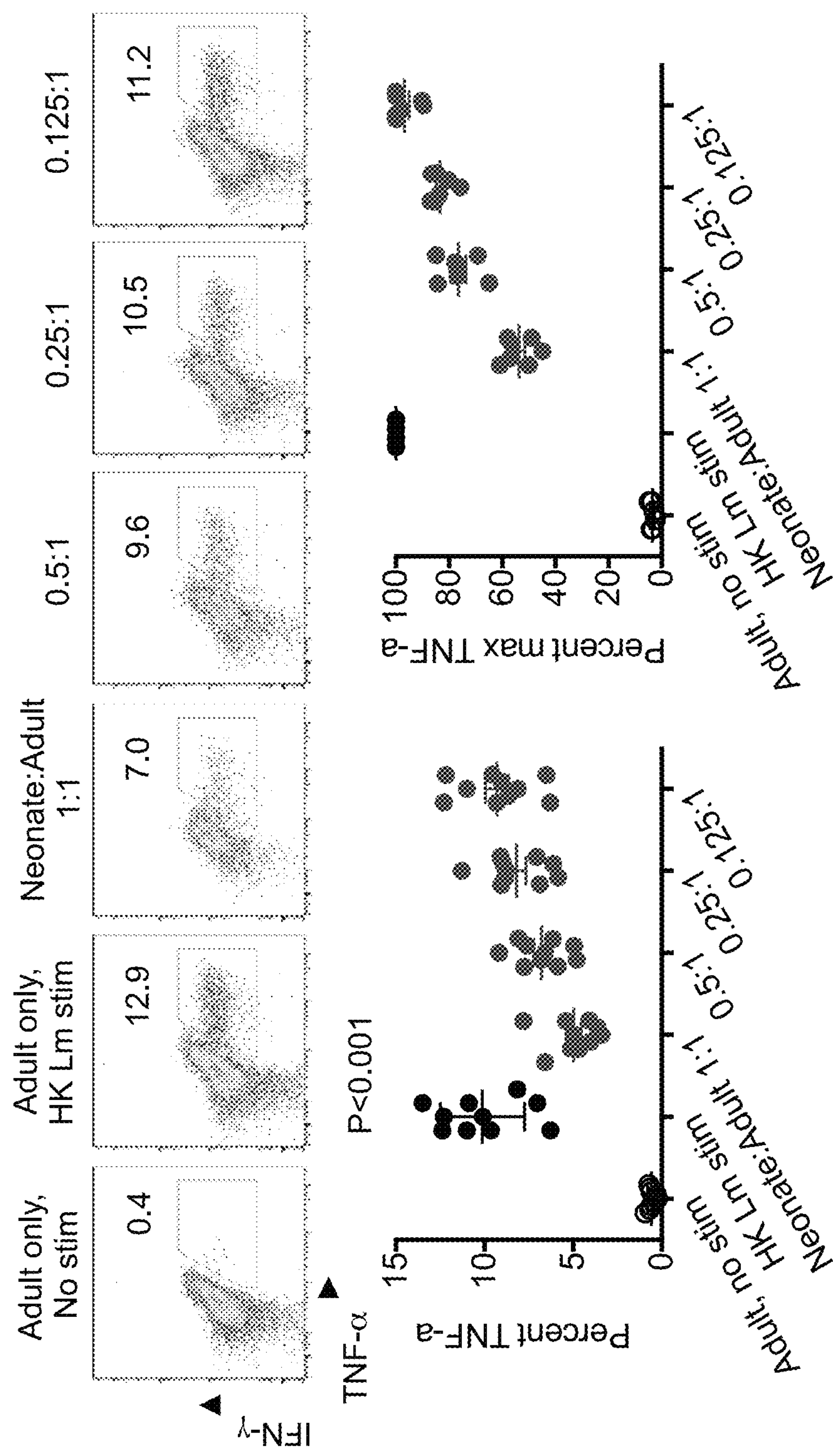
Figure 2C:
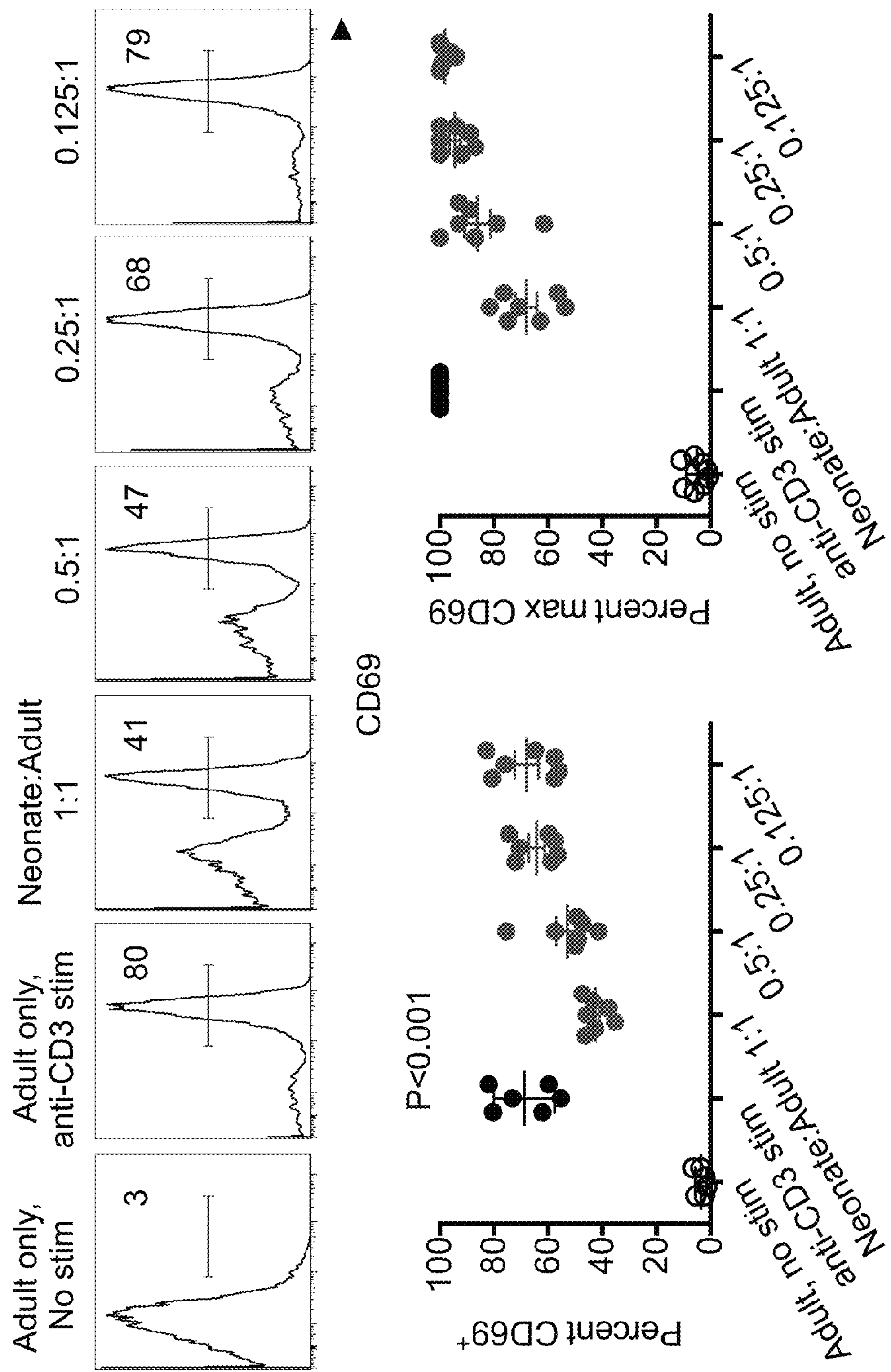

Neonatal Splenocytes Suppress the Activation of Adult Immune Cells in Co-Culture (FIGS. 2A-C).

FIG. 2A. TNF-α or IL-6 accumulation for day 6 neonate or adult splenocytes individually or in co-culture together after stimulation with heat killed Lm for 72 hours.

FIG. 2B. Representative plots, percentage, and normalized values illustrating TNF-α production by $CD11b^+$ cells among adult splenocytes after stimulation with heat killed Lm, and co-culture with the each ratio of splenocytes from day 6 neonatal mice.

FIG. 2C. Representative plots, percentage, and normalized values illustrating CD69 expression by $CD8^+$ cells among adult splenocytes after stimulation with anti-CD3 antibody, and co-culture with the each ratio of splenocytes from day 6 neonatal mice. Each data point represents the results from an individual mouse, representative of three independent experiments. Bar, mean±one standard error.

$CD71^+Ter119^+$ Neonatal Splenocytes Mediate Immune Suppression (FIGS. 3A-D).

Figure 3A:
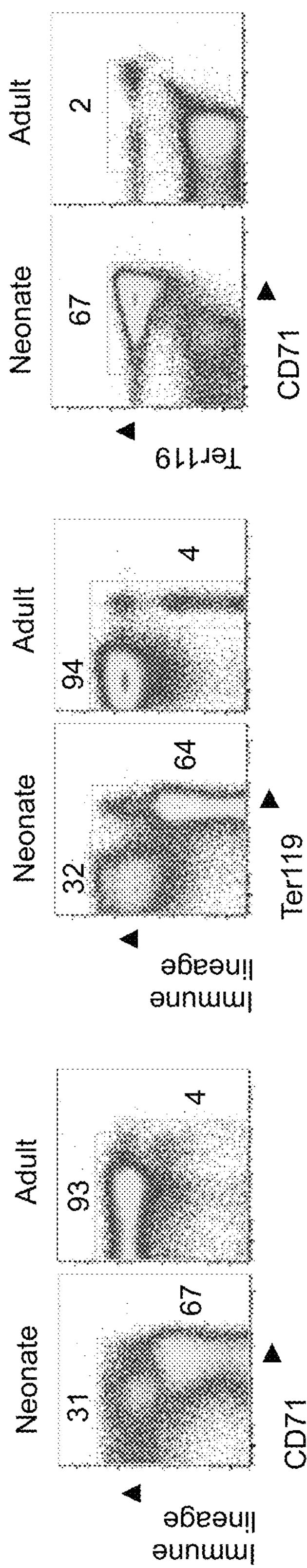

FIG. 3A. Representative plots showing percent immune cell lineage ($CD4^+$, $CD8^+$, $CD11b^+$, $CD11c^+$, $B220^+$, and $NK1.1^+$), $CD71^+$ and $Ter119^+$ cells among day 6 neonate and adult splenocytes.

Figure 3B:
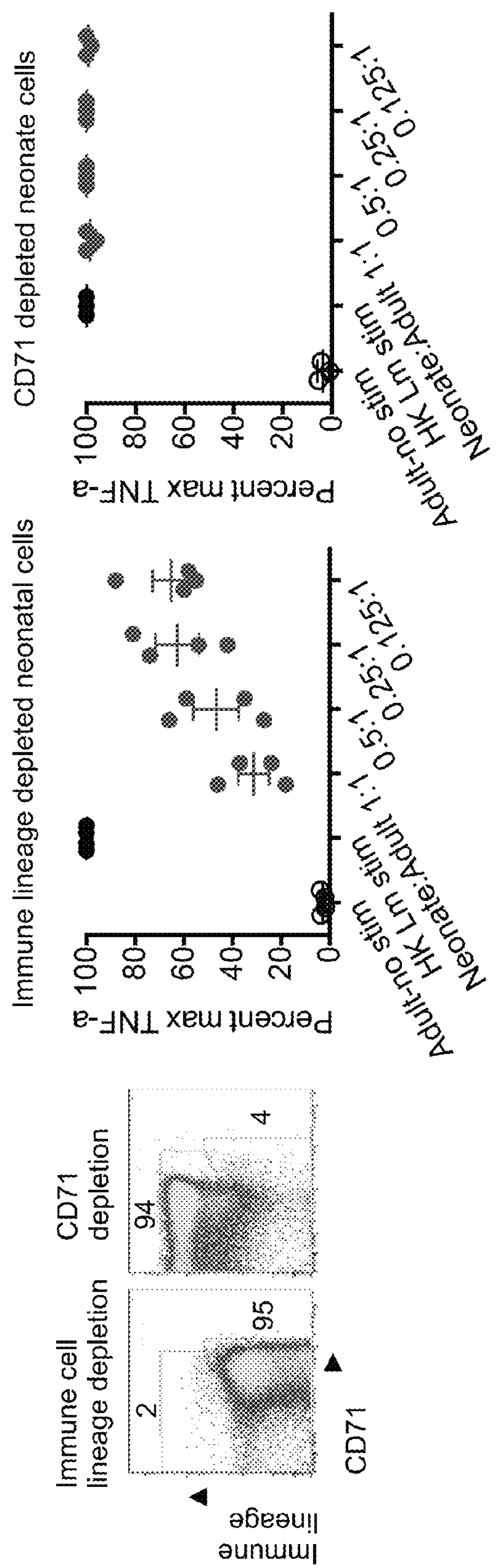

FIG. 3B. Representative plots illustrating the purity of $CD71^+$ or immune lineage neonate splenocytes after negative selection, and normalized values showing percent maximal TNF-α production by $CD11b^+$ adult splenocytes stimulated with heat killed Lm, and co-culture with each ratio of immune lineage (CD4, CD8, CD11b, CD11c, B220, and NK1.1) or CD71 depleted neonatal splenocyte cells.

Figure 3C:
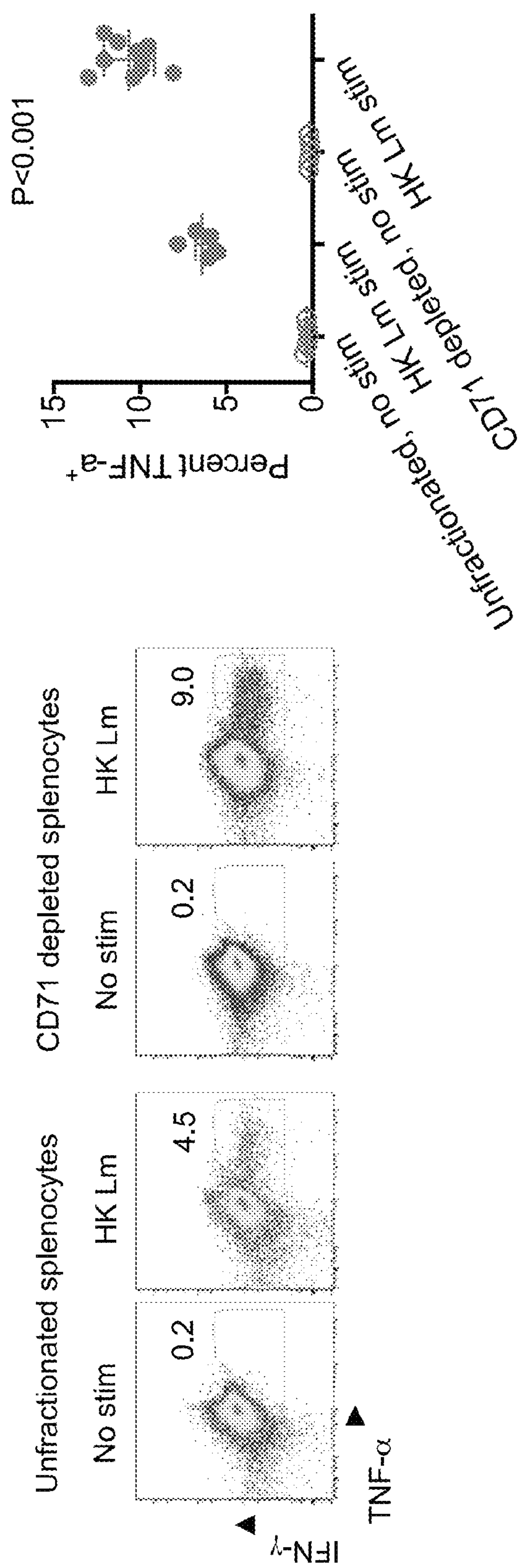

FIG. 3C. TNF-α production by $CD11b^+$ cells among unfractionated or CD71 cell depleted neonatal splenocytes after stimulation with heat killed Lm.

Figure 3D:
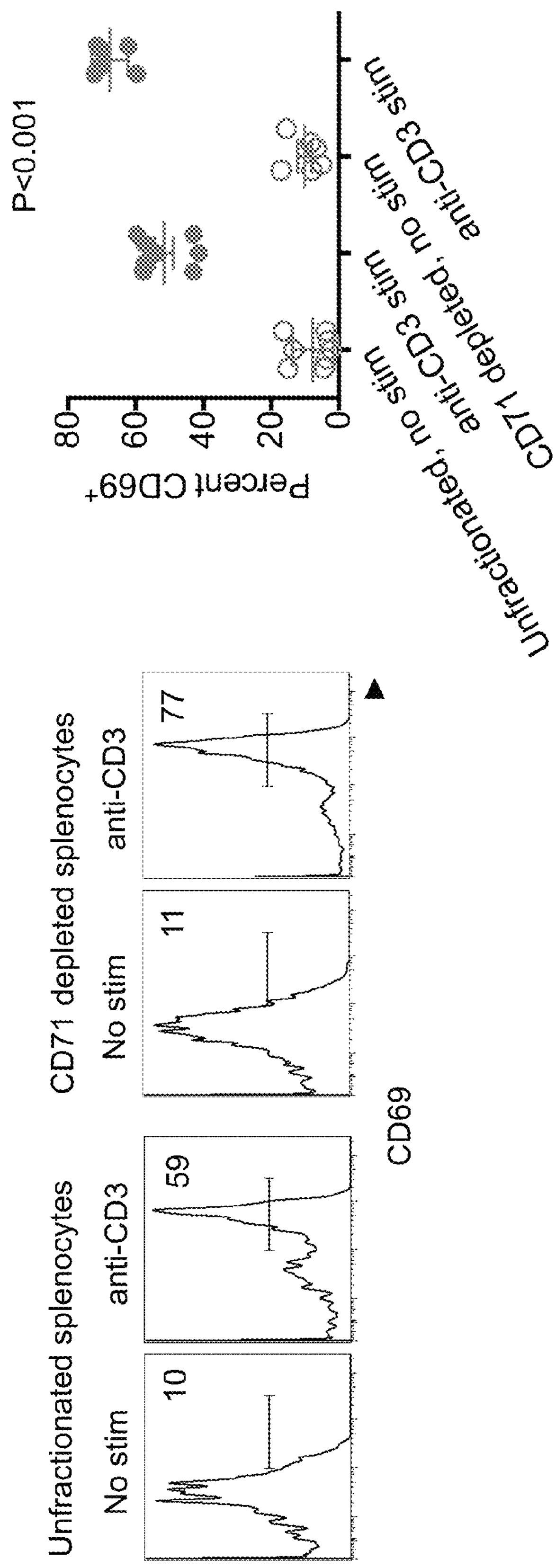

FIG. 3D. CD69 expression by $CD8^+$ cells among unfractionated or CD71 cell depleted neonatal splenocytes after stimulation with anti-CD3 antibody. Each data point represents the results from an individual mouse, representative of three independent experiments. Bar, mean±one standard error.

CD71 Cell Depletion Restores Host Defense Against Infection in Neonates (FIGS. 4A-D).

Figure 4A:
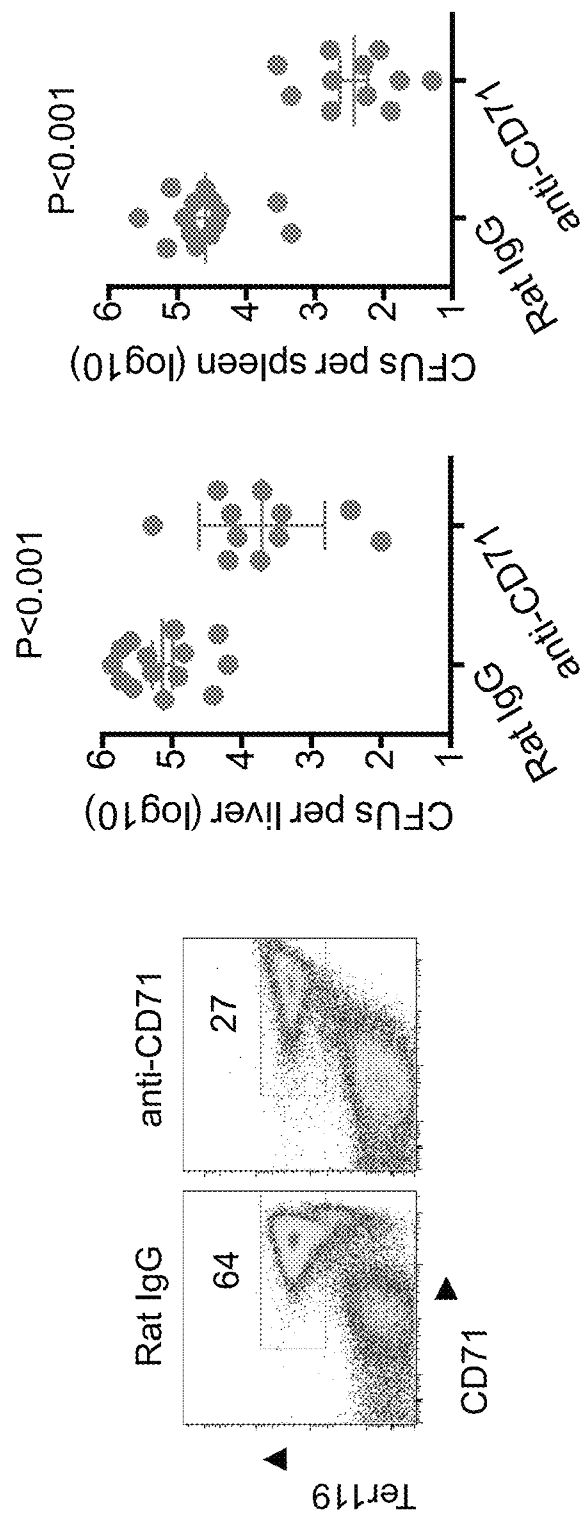

FIG. 4A. Representative plots showing percent $CD71^+$ $Ter119^+$ cells among splenocytes, and number of recoverable bacteria 48 hours after infection for anti-CD71 or isotype antibody treated neonatal mice.

Figure 4B:
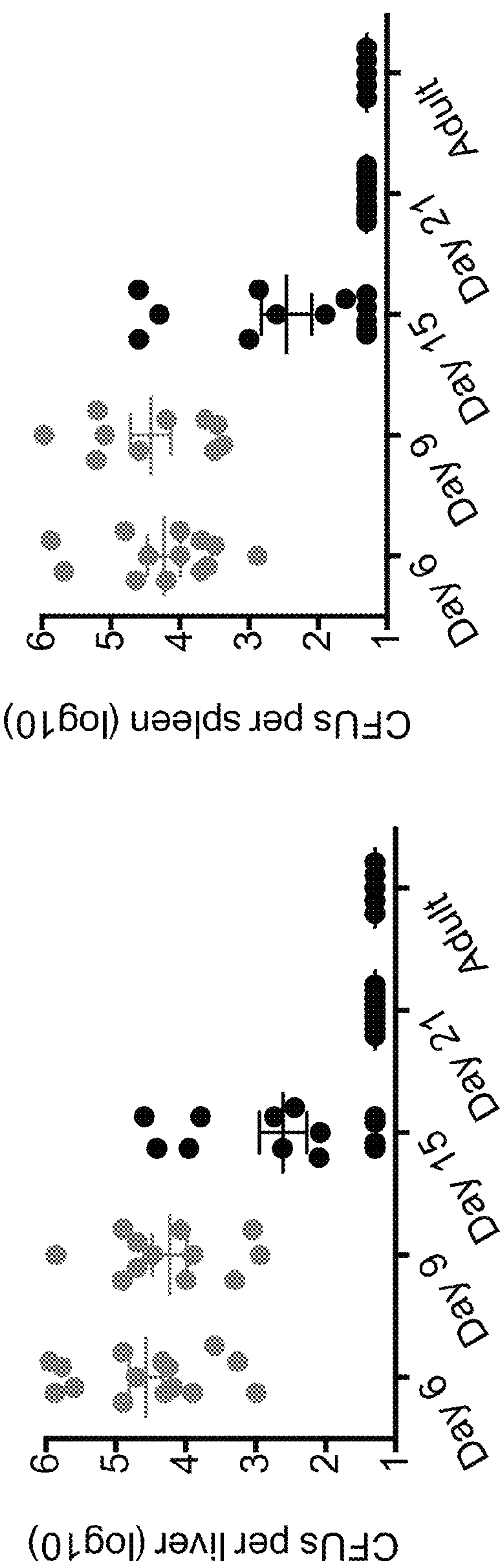

FIG. 4B. Number of recoverable bacteria for mice in each age group 48 hours after infection.

Figure 4D:
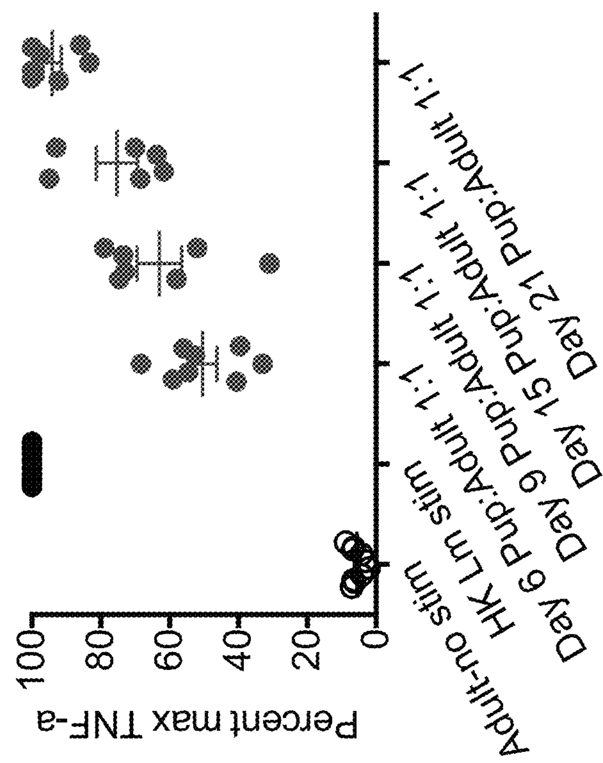
Figure 4C:
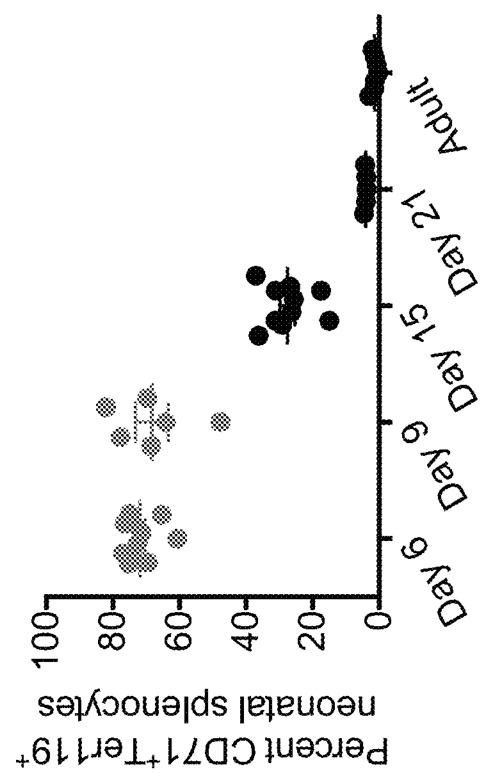

FIG. 4C. Percent $CD71^+Ter119^+$ erythroid cells among splenocytes for mice in each age group.

FIG. 4D. Normalized values illustrating TNF-α production by adult CD11b+ cells after stimulation with heat killed Lm, and co-culture with an 1:1 ratio of splenocytes from mice in each age group. Each data point represents the results from an individual mouse, representative of three independent experiments each with similar results. Bar, mean±one standard error.

Figure 5:
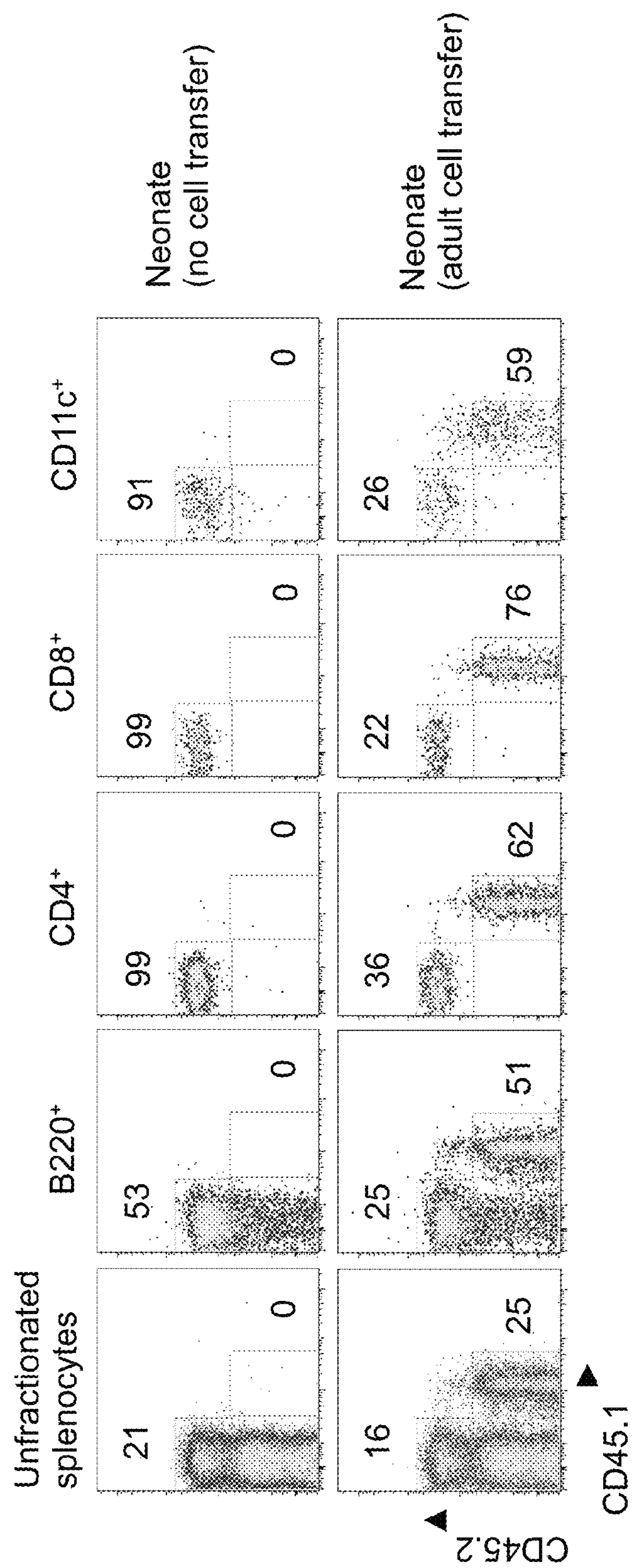

FIG. 5. Adoptively transferred adult $CD45.1^+$ splenocytes are retained in neonatal mice. Representative plots show the percent adult $CD45.1^+$ donor compared with endogenous neonatal $CD45.2^+$ cells among unfractionated splenocytes or each specific cell subset 48 hours after transfer into 5 day old neonatal mice.

Figure 6:
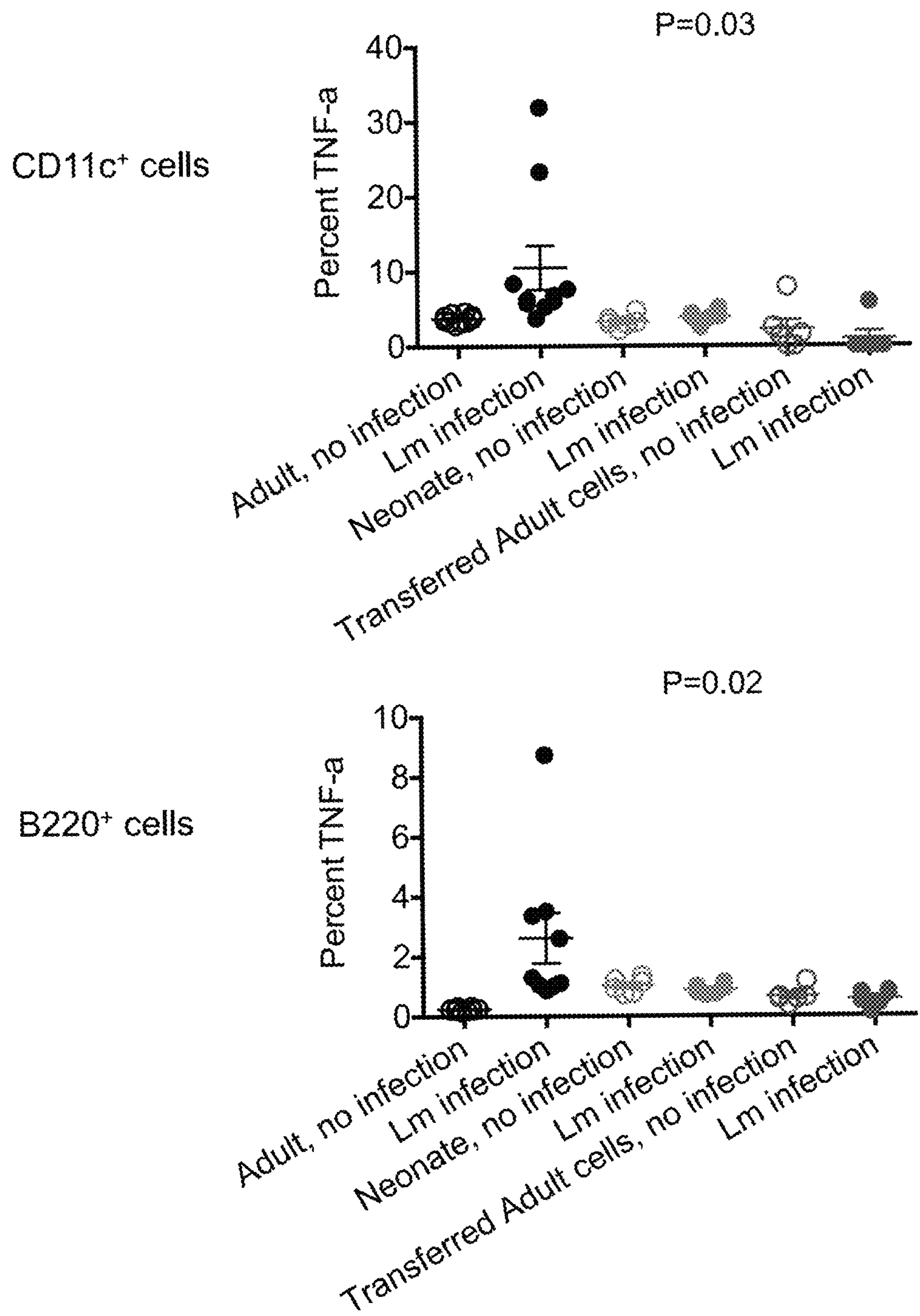

FIG. 6. Blunted TNF-α production among adult $CD11c^+$ and $B220^+$ cells after adoptive transfer into neonatal mice. Percent TNF-α cytokine producing cells after Lm infection in adult or day 6 neonatal mice containing adoptively transferred adult cells. Forty-eight hours after infection, splenocytes from infected mice were harvested, cultured in media containing brefeldin A for 4 hours, and then subjected to cell surface and intracellular cytokine staining. Bar, mean±one standard error.

Figure 7:
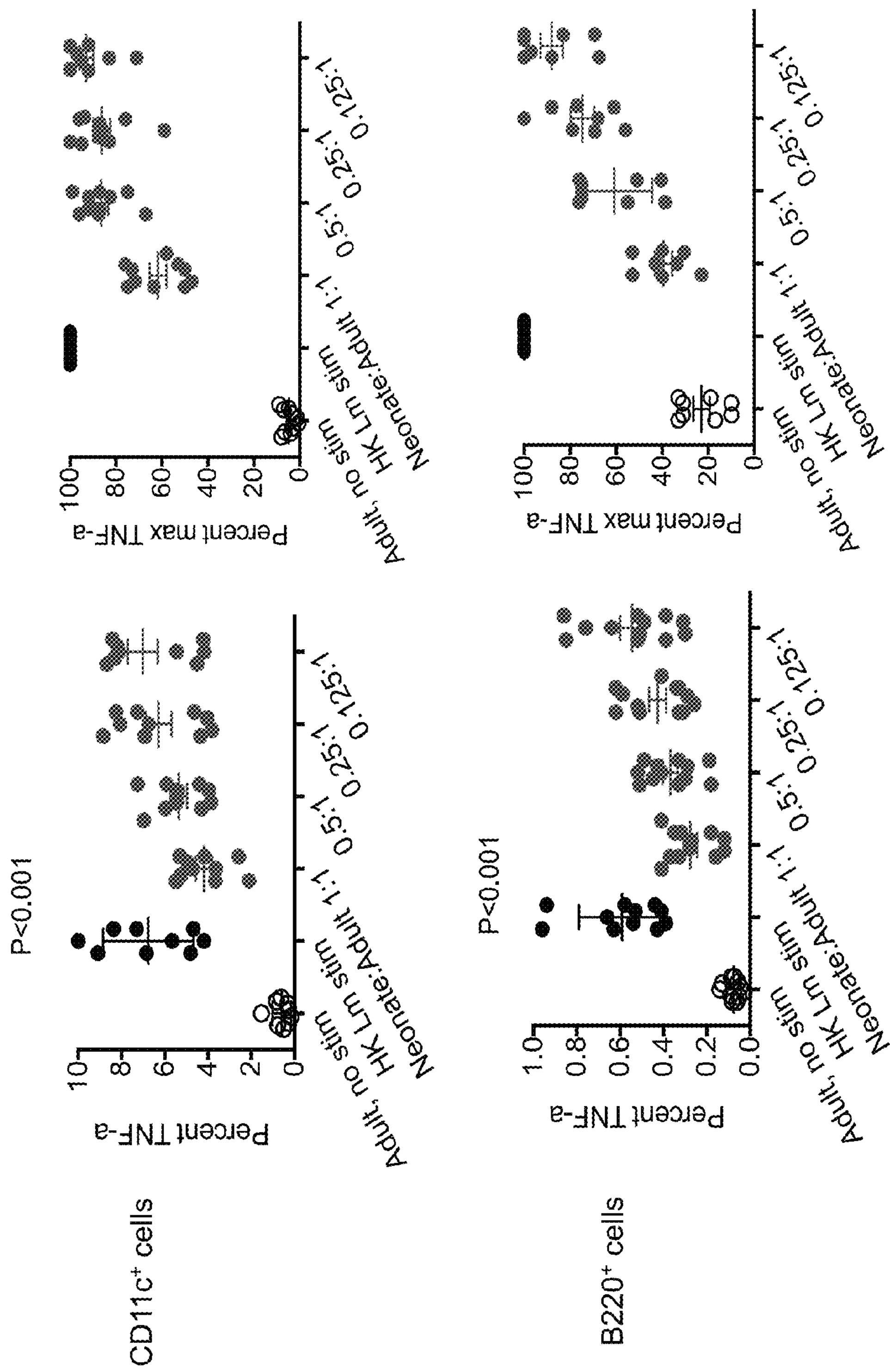

FIG. 7. Neonatal splenocytes suppress TNF-α production by adult $CD11c^+$ and $B220^+$ cells in co-culture. Percent and normalized values between individual experiments illustrating TNF-α cytokine production by $CD11c^+$ and $B220^+$ adult cells after stimulation with heat killed Lm, and co-culture with the indicated ratio of neonatal splenocyte cells. Bar, mean±one standard error.

Figure 8:
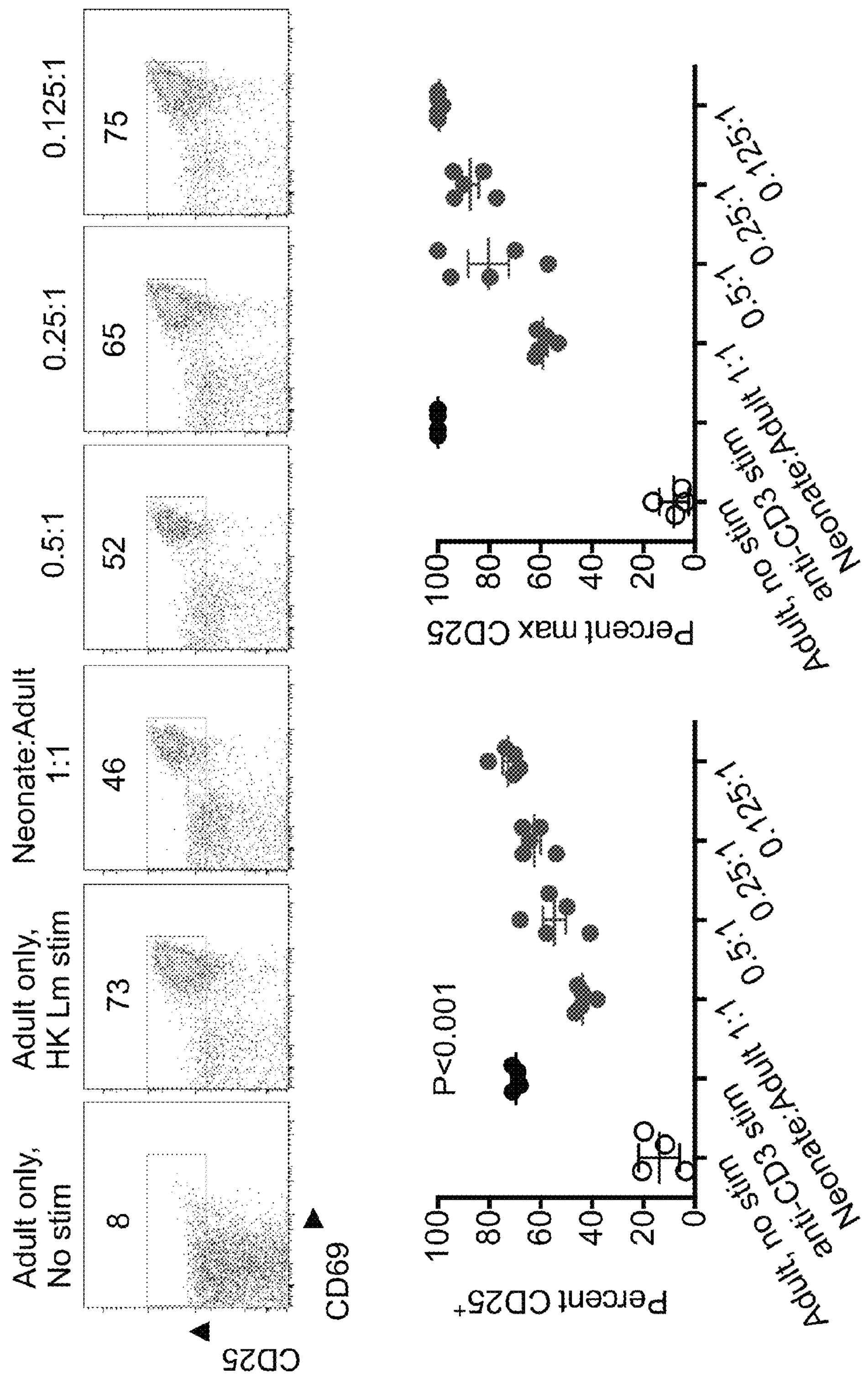

FIG. 8. Neonatal splenocytes suppress the activation of adult T cells in co-culture. Representative plots, percentage, and normalized values between individual experiments illustrating CD25 expression by $CD8^+$ cells among adult splenocytes after stimulation with anti-CD3 antibody, and co-culture with the each ratio of splenocytes from day 6 neonatal mice. Bar, mean±one standard error.

Figure 9:
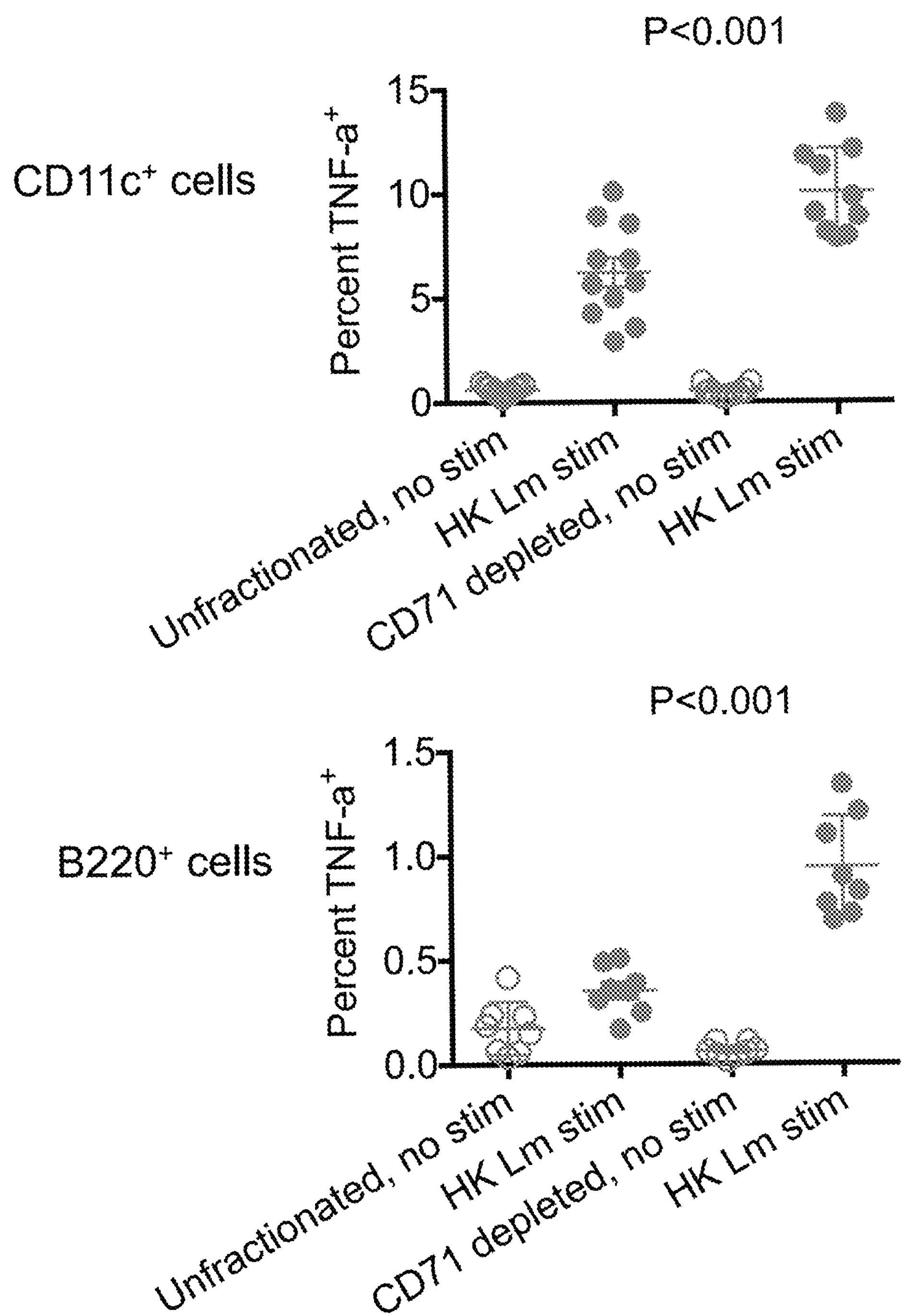

FIG. 9. Depletion of $CD71^+$ cells invigorates TNF-α production by neonatal $CD11c^+$ and $B220^+$ cells. Percent TNF-α cytokine producing $CD11c^+$ or $B220^+$ cells after stimulation with heat killed Lm among unfractionated or CD71 cell depleted neonatal splenocytes. Bar, mean±one standard error.

Figure 10:
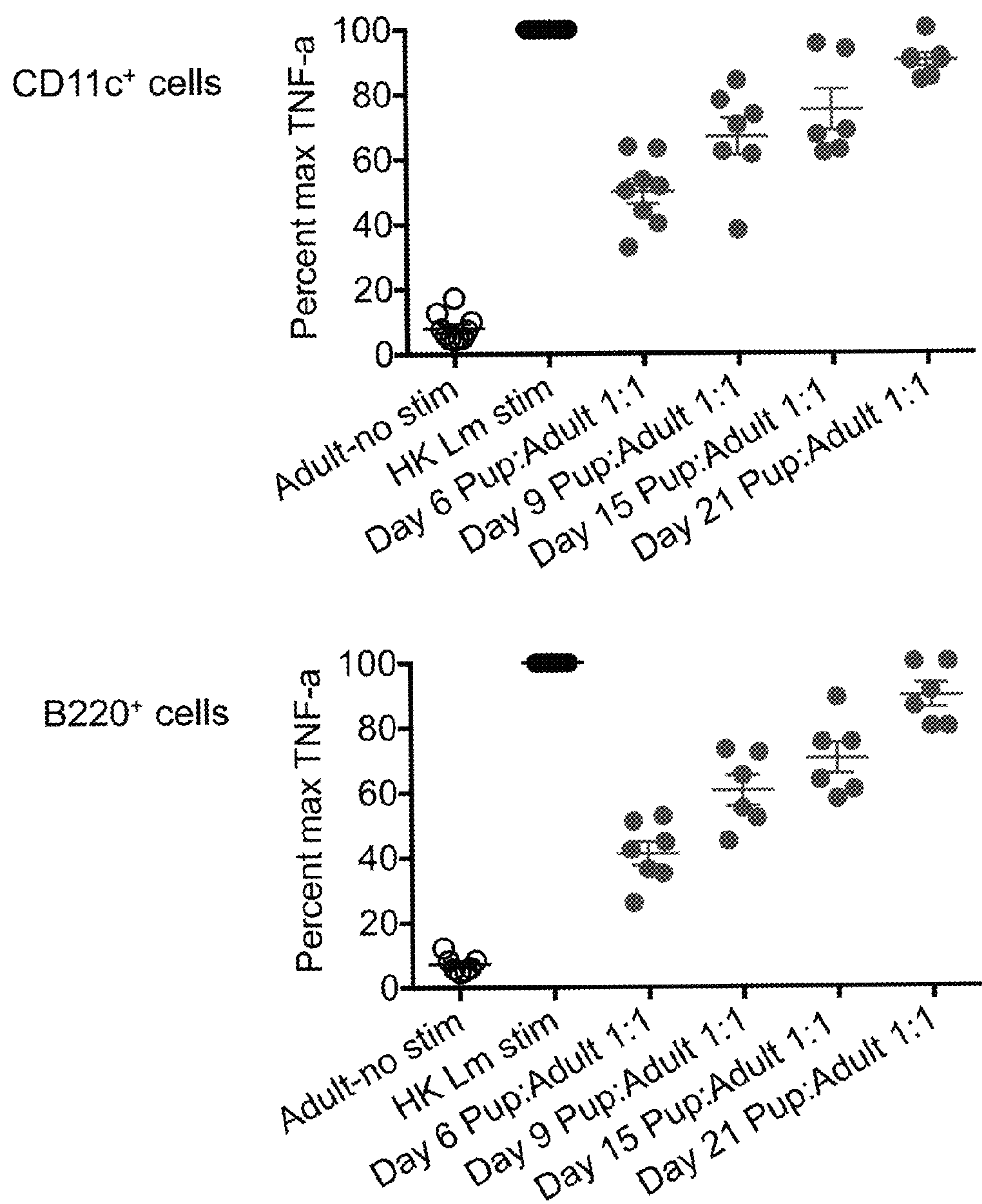

FIG. 10. Progressive decline in suppressive potency among neonatal splenocytes with postnatal development. Normalized values between individual experiments illustrating TNF-α production by $CD11c^+$ and $B220^+$ adult cells after stimulation with heat killed Lm, and co-culture with a 1:1 ratio of splenocytes from day 6, day 9, day 15, and day 21 old pups. Bar, mean±one standard error.

DETAILED DESCRIPTION

The physiologically enriched proportion of $CD71^+$ $Ter119^+$ erythroid cells in neonates actively suppresses the activation of neonatal, as well as adult immune effector cells, and inhibits host defense against the perinatal pathogen *Listeria monocytogenes* (Lm)[12]. Production of innate protective cytokines and cellular activation were blunted for adult immune cells adoptively transferred into newborn mice, or after co-culture with neonatal splenocytes. In turn, depletion of $CD71^+$ erythrocyte precursor cells eliminated the suppressive properties of neonatal cells and restored resistance against infection. Furthermore, the progressive decline in $CD71^+Ter119^+$ cells during postnatal development paralleled the loss of these immune suppressive properties and engraftment of host defense to adult levels. The enriched proportion of $CD71^+Ter119^+$ erythroid "suppressor" cells in neonates actively inhibits protective immunity. These findings challenge the existing notion that infection susceptibility in neonates is due to immune cell intrinsic defects[1-3], and instead highlight developmentally essential processes that may inadvertently mitigate innate protection against infection.

Infants within the first few weeks after birth are highly susceptible to disseminated and often fatal infection. Although many distinctions that include diminished production of innate inflammatory cytokines, skewed T helper type 2 adaptive responses, blunted cellular activation, or reduced numbers of mature immune effector and antigen presenting cells have been described[1-3], the degree of neonatal cell hyporesponsiveness also varies markedly depending on stimulation conditions[4-11]. Thus, with neonatal immune cells having the potential for activation, a more unifying explanation for why newborns remain susceptible to infection is needed.

Figure 1A:
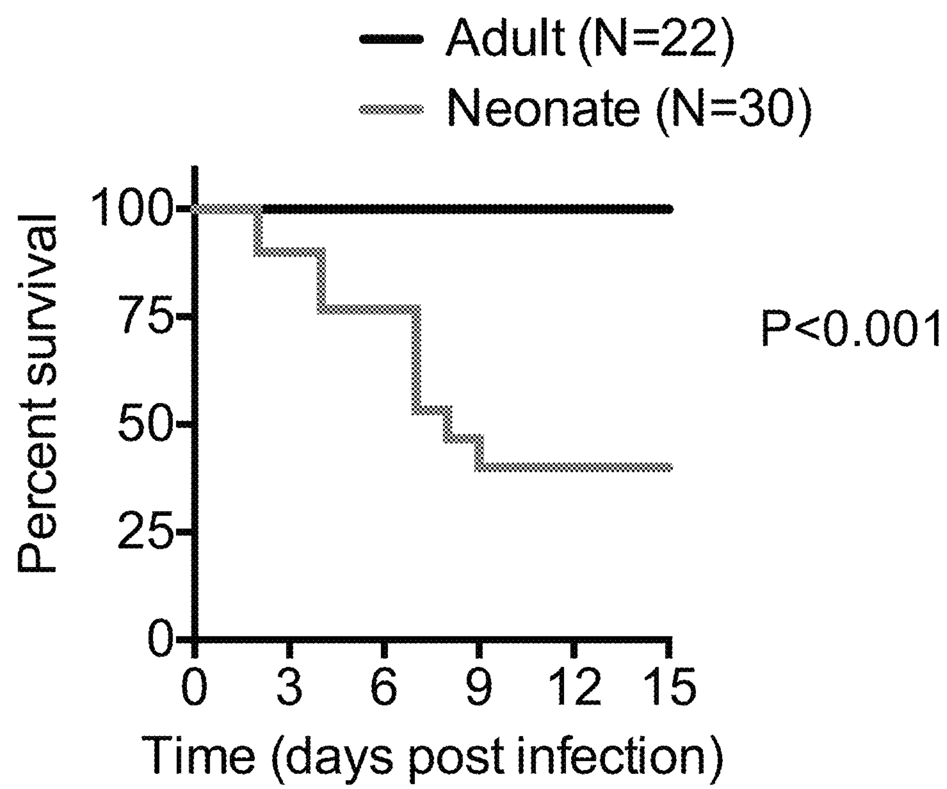
FIG. 1A. Percent survival among day 6 neonate or 8 week adult mice after intraperitoneal inoculation with 200 Lm CFUs.
Figure 1B:
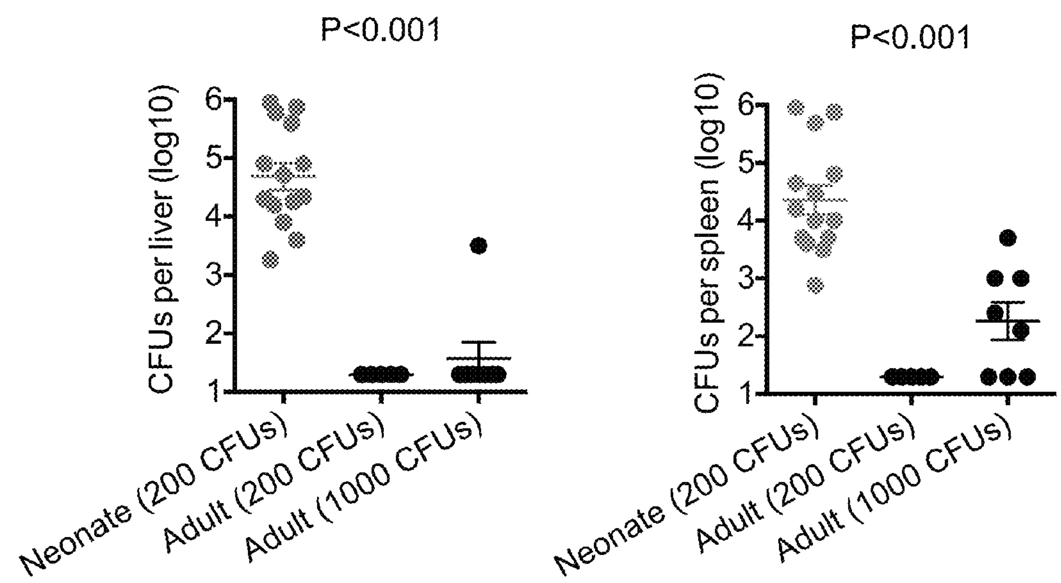
FIG. 1B. Number of recoverable bacteria 48 hours after infection with each Lm dosage in neonate or adult mice.

It was discovered the sharply increased susceptibility to disseminated infection with the intracellular bacterium *Listeria monocytogenes* (Lm) for human newborns is recapitulated in neonatal mice (FIG. 1A)[12]. Given the delayed immunological development at birth for mice compared with humans[13,14], 6 day neonate in comparison with 8 week old adult mice were utilized. Consistent with these profound reductions in survival, greater than 10,000-fold more recoverable Lm were found in the liver and spleen of neonate compared with adult mice within the first 48 hours after infection (FIG. 1B). Furthermore, the susceptibility in neonates was maintained after adjusting the Lm dosage used for adult mice proportional to their increased weight (FIG. 1B). Thus, neonatal mice, like newborn humans, are intrinsically more susceptible to disseminated infection.

Figure 1C:
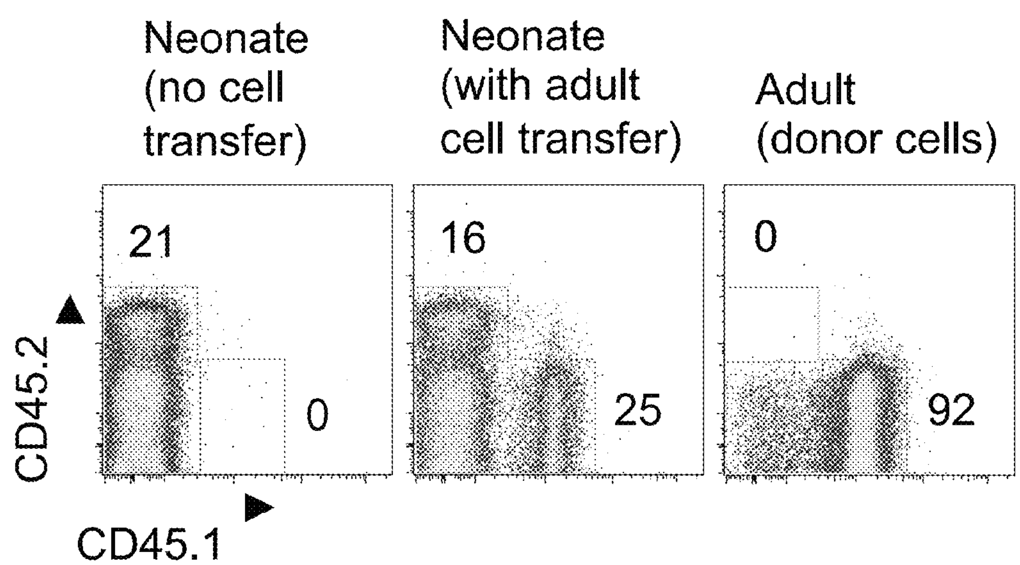
FIG. 1C. Percent adult $CD45.1^+$ donor cells among neonatal $CD45.2^+$ splenocytes 48 hours after adoptive cell transfer.
Figure 1D:
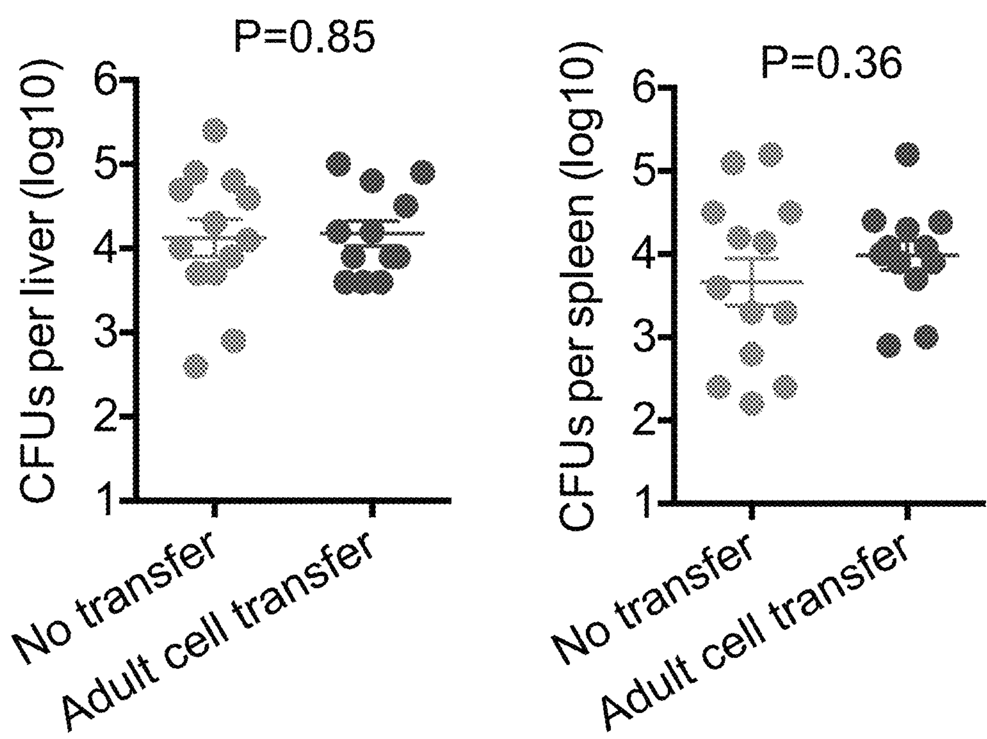
FIG. 1D. Number of recoverable bacteria in day 6 neonatal mice transferred adult splenocyte cells or no transfer controls 48 hours after infection.

To investigate if susceptibility in neonates is caused by naturally occurring qualitative diminutions in immune cell function or quantitative reductions in immune cells, the impact of adoptively transferred splenocytes from adult mice on subsequent Lm susceptibility in neonates was evaluated. These studies utilized cells derived from immunologically identical, but congenically marked CD45.1 adult mice that are distinguished from CD45.2 neonatal immune cells so that transferred cells could be easily identified (FIG. 1C and FIG. 5). It was predicted that infection susceptibility in neonates is caused by immune cell hyporesponsiveness or reduced absolute numbers of protective immune cells, donor cells from resistant adult mice would restore protection. Interestingly, and in striking contrast to this prediction, adoptive transfer of adult splenocyte cells one day prior to infection had no significant impact on Lm bacterial burden in neonatal mice (FIG. 1D).

Figure 1E:
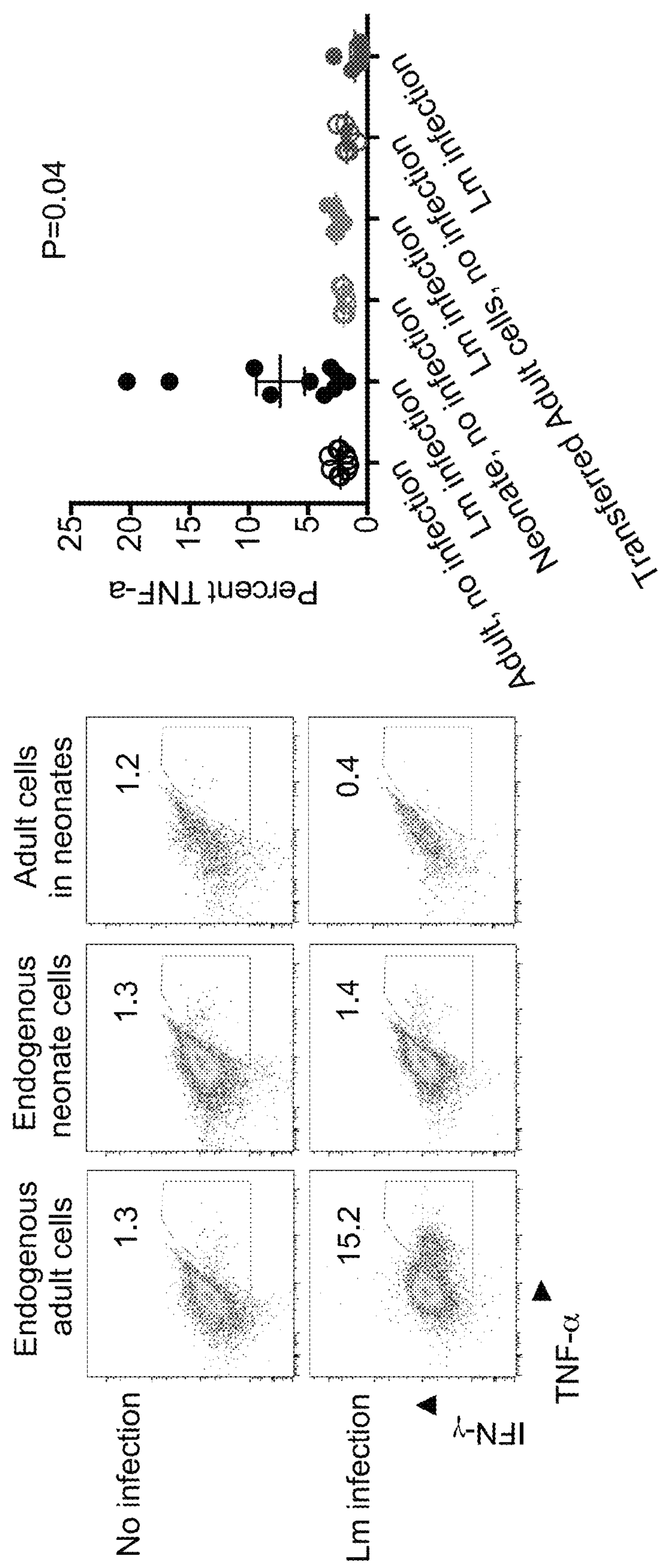
FIG. 1E. TNF-α production by $CD11b^+$ adult, neonatal, or adult cells within neonates 48 hours after Lm infection or no infection controls. Each data point represents the results from an individual mouse, representative of three independent experiments. Bar, mean±one standard error.

Given these unexpected results, the degree of activation for adult immune cells in Lm infected neonatal mice was also investigated. Since differences in susceptibility between neonates and adults become apparent within the first 48 hours after infection, production of innate protective cytokines such as TNF-α, IFN-γ, and IL-12 essential for protection early after Lm infection[15-18] was focused on in particular. It was found TNF-α production became uniformly extinguished among adult $CD11b^+$ monocyte/macrophage, $CD11c^+$ dendritic cells, and $B220^+$ lymphocytes after infection in neonate compared with adult mice, and was reduced to background levels similar to neonatal cells (FIG. 1E and FIG. 6). Comparatively under these infection conditions, neither IFN-γ nor IL-12 were produced above background levels (data not shown). Although this approach may not recapitulate the micro-anatomic distribution of all immune cells in lymphoid and other tissues, these findings nevertheless suggest infection susceptibility in neonates might not simply reflect immune cell intrinsic defects, but instead the result of active suppression within the neonatal environment.

To investigate the potential immune suppressive properties of neonatal cells, cytokine production by adult cells in co-culture with neonatal splenocytes was evaluated. Consistent with blunted responses among neonatal cells stimulated using various purified microbial ligands[1-3,8,9], TNF-α and IL-6 production were each sharply reduced among neonate compared with adult cells after stimulation with heat-killed Lm (FIG. 2A). Remarkably, when an equal ratio of neonatal splenocytes was added to adult splenocytes in co-culture, levels of both TNF-α and IL-6 declined significantly compared with cultures containing only adult cells (FIG. 2A). To more precisely characterize these suppressive properties, intracellular cytokine and cell surface staining was used to define the adult splenocyte subset(s) suppressed from cytokine production. Using a similar approach for identifying adult cells among neonatal splenocytes after adoptive transfer (FIG. 1C), the CD45.1/CD45.2 congenic markers were used to discriminate adult from neonatal cells in co-culture. Similar to Lm infection in vivo, TNF-α was produced almost exclusively by adult $CD11b^+$, $CD11c^+$, and $B220^+$ cells after stimulation with heat killed Lm; and co-culture with neonatal splenocytes, in a dose dependent fashion, efficiently suppressed cytokine production by each cell subset (FIG. 2B and FIG. 7). These suppressive properties also extended to T cells because co-culture with neonatal splenocytes, in a dose dependent fashion, also blunted CD69 and CD25 expression among adult T cells after anti-CD3 antibody stimulation (FIG. 2C and FIG. 8). Thus, co-culture with neonatal splenocytes recapitulates the suppression imposed upon adult immune cells after adoptive transfer into neonates.

The neonatal cell subset that confers these newfound suppressive properties was investigated. Compared with adult splenocytes where ~93% of cells express established immune cell lineage defining markers CD4, CD8, CD11b, CD11c, B220, and NK1.1, less than 35% of day 6 neonatal splenocytes stain positive for these markers (FIG. 3A). Reciprocally, immune lineage negative cells among neonatal splenocytes almost uniformly co-expressed transferrin receptor (CD71) and erythroid lineage (Ter119) markers (FIG. 3A). These results parallel the elevated percentage of cells that do not express the CD45.2/CD45.1 leukocyte common antigens among neonate compared with adult splenocytes (FIG. 1C), and are consistent with an enriched proportion of erythrocyte progenitor cells within the lymphoid tissue of fetal and neonatal mice[19], and in human cord blood[20].

To determine which cell subset confers suppression, neonatal splenocytes were fractionated by negative selection using anti-CD71 or a cocktail of anti-CD4, CD8, CD11b, CD11c, B220, and NK1.1 antibodies, and the suppressive potential of each subset evaluated after co-culture with adult splenocytes. This analysis showed suppression by neonatal cells was completely eliminated by depletion of $CD71^+$ cells (FIG. 3B). By contrast, the combined depletion of CD4, CD8, CD11b, CD11c, B220, and $NK1.1^+$ cells not only retained, but exaggerated the suppressive properties of the remaining $CD71^+$ neonatal splenocytes (FIG. 3B). This augmented potency was most likely caused by the ~1.5-fold enriched proportion of $CD71^+$ cells after depletion of CD4, CD8, CD11b, CD11c, B220, and $NK1.1^+$ cells because suppressive function diminished in parallel with unfractionated neonatal splenocytes when reduced ratios of neonatal cells were used in co-culture (FIG. 3B, 2B). Extending this analysis, the role of $CD71^+$ cells in suppressing neonatal immune cell activation was also investigated. It was found that $CD71^+$ cell depletion among neonatal splenocytes unleashed significantly more TNF-α production among remaining CD11b, CD11c, and B220 cells (FIG. 3C and FIG. 9), and CD69 expression among neonatal T cells (FIG. 3D). Together, these results show enriched $CD71^+Ter119^+$ erythroid cells in neonates inhibit immune cell activation.

Finally, the degree whereby these newfound immune suppressive properties for $CD71^+Ter119^+$ erythroid cells control infection susceptibility in neonates was addressed using two complementary approaches. First, the selective down-regulation of CD71 on mature red blood cells[21,22] was used so that unlike depletion using anti-Ter119 antibody that uniformly caused neonatal demise from hemolysis within 8-12 hours, anti-CD71 antibody administration did not negatively impact health (data not shown). Although only ~60% $CD71^+Ter119^+$ cells were depleted, significant reductions in Lm bacteria were found in anti-CD71 compared with isotype antibody treated mice (FIG. 4A). Secondly, the level of $CD71^+Ter119^+$ cells and infection susceptibility throughout postnatal development was evaluated. It was investigated whether enriched $CD71^+Ter119^+$ cells play dominant roles in compromising host defense in neonates, engraftment of immunity to adult levels would parallel the physiological disappearance of these cells. This notion was supported by sustained susceptibility for 9 day compared with 6 day old mice that contain indistinguishably elevated CD71⁺Ter119⁺ splenocytes and high Lm pathogen burdens (FIG. 4B,C). With increasing postnatal development, the progressive decline in CD71⁺Ter119⁺ cells directly paralleled significant reductions in infection susceptibility. Recoverable Lm was reduced 100-fold for 14 day old mice containing ~60% reductions in CD71⁺Ter119⁺ cells, and fell to below the limits of detection for 21 day old mice where CD71⁺Ter119⁺ cells declined to levels comparable to adult mice (FIG. 4B,C). Moreover, this progressive engraftment of immunity to adult levels with the decline in CD71⁺Ter119⁺ cells also directly paralleled the loss of suppressive function among splenocytes (FIG. 4D and FIG. 10). Thus, antibody induced depletion or the physiological disappearance of CD71⁺ Ter119⁺ erythroid cells during postnatal development each restore host defense against infection. Together, these results show the naturally enriched proportion of immune suppressive CD71⁺Ter119⁺ erythroid cells in neonates dictates infection susceptibility.

Given the increasingly appreciated in utero mixing and bi-directional cell transfer between mother and fetus in mammalian pregnancy[14,23-25], compelling suppressive mechanisms are likely engaged on both sides of the placenta to ensure semi-allogeneic foreign tissues are not rejected. For maternal tolerance to the developing fetus, the induction and sustained expansion of immune suppressive regulatory CD4 cells by the mother is essential[26-29]. Although neonatal Foxp3⁺ CD4 cells were not directly investigated in these studies, these cells are unlikely to play dominant roles in mitigating host defense that causes neonatal infection susceptibility because their elimination along with other immune lineage cells did not abrogate, but instead enhanced suppression by neonatal splenocytes (FIG. 3B).

These results indicate erythroid precursor cells with immune suppressive properties play critical roles in restraining undesired activation of maturing fetal immune cells in utero. In this regard, infection susceptibility caused by transient postnatal immune suppression from residual erythroid "suppressor" cells that rapidly decline within the first few weeks after birth may be relate to the active suppression of fetal immune responses. By extension, immune suppression from sustained extramedullary erythropoiesis in individuals with sickle-cell or other diseases that significantly shorten red blood cell life span can also explain their increased susceptibility to infection[30].

Some embodiments provide a method of augmenting an immune response in a subject in need thereof, comprising identifying the subject, and treating the subject to inhibit the immune suppressive effect of CD71⁺ cells.

The immune suppressive effect of CD71⁺ cells may be assessed using any suitable assay. For example, in some embodiments, the increased susceptibility to disseminated infection with Lm may be determined. In some embodiments, the suppressive effect on production of innate protective cytokines such as TNF-α, IFN-γ, and/or IL-12 among CD11b⁺ monocyte/macrophage, CD11c⁺ dendritic cells, and/or B220⁺ lymphocytes may be determined.

A subject in need of augmenting an immune response may be a subject with weakened immune systems, a subject that comes into contact with infected individuals, a subject under environmental, physical or psychological stress, or a combination of such factors. In some embodiments, a subject may have a weakened immune system due to being infected with HCV, HIV, tuberculosis, or other immune system compromising condition. In some embodiments, a subject may have a weakened immune system due to having cancer. In some embodiments, a subject may have a weakened immune system due undergoing chemotherapy or radiation therapy. In some embodiments, a subject may have a weakened immune system due to receiving a bone marrow transplant. In some embodiments, a subject in need of augmenting an immune response may come into contact with infected material.

The subject may be a mammal. For example, the subject may be a human. In some embodiments, a subject may be a neonate or newborn. In some embodiments, the newborn may be less than 21, 21, 23, 24, 25, 26, 27, 28, 29, or 30 days old. In some embodiments, the newborn may be greater than 1, 2, 3, 4, 5, 6, 7, 8, 9, or 10 days old.

In some embodiments, the method further comprises determining the level of CD71⁺ cells in the subject. In some embodiments, the level of CD71⁺ cells in the subject is elevated in comparison to a reference level. An elevated level of CD71⁺ cells in the subject in comparison to the reference level may indicate that the subject is in need of augmenting an immune response. The level of CD71⁺ cells in the subject may be determined by any suitable assays, including but not limited to, flow cytometry, ELISA, lateral flow based assay, etc. In some embodiments, an antibody that specifically binds to CD71 may be used for determining the level of CD71⁺ cells in the subject.

A variety of immune responses may be augmented using the methods disclosed herein. In some embodiments, the immune response to be augmented is a host defense against infection.

In some embodiments, treating the subject comprises administering to the subject an agent that specifically binds to CD71. In some embodiments, the agent that specifically binds to CD71 is an anti-CD71 antibody. In some embodiments, the anti-CD71 antibody is R17217. In some embodiments, the anti-CD71 antibody is C2F2.

In some embodiments, the treating the subject comprises depleting CD71⁺ cells from the subject. In some embodiments, the CD71⁺ cells are erythrocytes. In some embodiments, the erythrocytes are CD71⁺Ter119⁺ erythrocytes. In some embodiments, depleting CD71⁺ cells from the subject comprises administering to the subject an agent that reduces the level of CD71⁺ cells. In some embodiments, depleting CD71⁺ cells from the subject comprises administering to the subject an agent that reduces the level of CD71⁺ erythrocytes. In some embodiments, depleting CD71⁺ cells from the subject comprises administering to the subject an agent that reduces the level of CD71⁺Ter119⁺ erythrocytes.

The agent may be linked to a moiety that facilitates the depletion of the cells bound to the agent. For example, the agent may be bound to a bead, a magnetic microparticle, a fluorescent label, that may be used to deplete the cells bound to the agent. In some embodiments, the agent specifically binds to CD71. In some embodiments, the agent that specifically binds to CD71 is an anti-CD71 antibody.

In some embodiments, the depleting CD71⁺ cells from the subject comprises separating the CD71⁺ cells from the blood of the subject.

Some embodiments provide a method of identifying a modifier of an immune response, comprising providing CD71⁺ cells, providing an agent to the CD71⁺ cells, and assessing the ability of the agent to modify the immunosuppressive effect of the CD71⁺ cells. In some embodiment, the agent is a chemical compound. In some embodiment, the chemical compound is from a library. In some embodiment, the agent is an antibody. In some embodiment, the antibody is raised using $CD71^+$ cells as antigen. In some embodiment, the antibody is an anti-CD71 antibody.

Some embodiments provide a method of preventing, treating or ameliorating an infection in a subject, comprising administering to the subject an agent that reduces the level of $CD71^+$ cells in the subject.

Subjects may have come into contact with infected individuals, individuals under environmental, physical or psychological stress, or a combination of such factors. In some embodiments, the subject may have been infected with HCV, HIV, tuberculosis, or other infectious material. In some embodiments, the subject may have an infection due to having cancer. In some embodiments, the subject may have an infection due undergoing chemotherapy or radiation therapy. In some embodiments, the subject may have an infection due to receiving a bone marrow transplant. In some embodiments, the subject may come into contact with infectious material. In some embodiments, the subject may be a neonate or newborn.

In some embodiments, the agent specifically binds to CD71. In some embodiments, the agent that specifically binds to CD71 is an anti-CD71 antibody. In some embodiments, the anti-CD71 antibody is a humanized antibody. In some embodiments, the anti-CD71 antibody is a human antibody. In some embodiments, the agent downregulates the level of $CD71^+$ cells. In some embodiments, the method further comprises identifying the subject at risk for the infection. In some embodiments, the method further comprises determining the level of $CD71^+$ cells in the subject. In some embodiments, the level of $CD71^+$ cells in the subject is elevated in comparison to a reference level.

Some embodiments provide a composition for modifying an immune response comprising an agent identified by methods disclosed and described herein and a pharmaceutically acceptable carrier. In some embodiments, the agent is a chemical compound. In some embodiments, the agent is an antibody.

Some embodiments provide a method of boosting an immune response in neonates and newborns comprising administering to a neonate or newborn in need thereof an anti-CD71 antibody. In some embodiments, the newborn may be less than 21, 21, 23, 24, 25, 26, 27, 28, 29, or 30 days old. In some embodiments, the newborn may be greater than 1, 2, 3, 4, 5, 6, 7, 8, 9, or 10 days old.

Some embodiments provide a method of boosting an immune response in neonates and newborns comprising administering to a neonate or newborn in need thereof an anti-CD71 antibody whereby the immunosuppressive effect of $CD71^+$ cells is inhibited.

Some embodiments provide a method of identifying an immune response stimulating agent, comprising: providing $CD71^+$ cells; providing an agent; and assaying the ability of said agent to suppress the immunosuppressive effect of $CD71^+$ cells. In some embodiments, the agent may be an anti-CD71 antibody.

Some embodiments provide a pharmaceutical composition for reducing an immune response in a subject comprising a $CD71^+$ stimulator and a pharmaceutically acceptable carrier.

Some embodiments provide a method of screening a compound library comprising: (a) obtaining a library comprising a plurality of compound structures; (b) obtaining $CD71^+$ cells; and (c) identifying compounds which inhibit production of TNF-$\alpha$.

Some embodiments provide a method of ameliorating, preventing or treating an infection in an individual, the method comprising administering to the individual in need thereof an effective amount of a compound identified by the method of screening a compound library as disclosed and described herein.

Some embodiments provide a method of ameliorating, preventing or treating an infection in an individual, the method comprising administering to the individual an effective amount of an agent that down regulates $CD71^+$ cells.

Individuals in need of augmenting an immune response at risk for infection may be individuals with weakened immune systems, individuals that come into contact with infected individuals, individuals under environmental, physical or psychological stress, or a combination of such factors. In some embodiments, the individual may have a weakened immune system due to being infected with HCV, HIV, tuberculosis, or other immune system compromising condition. In some embodiments, the individual may have a weakened immune system due to having cancer. In some embodiments, the individual may have a weakened immune system due undergoing chemotherapy or radiation therapy. In some embodiments, the individual may have a weakened immune system due to receiving a bone marrow transplant. In some embodiments, the individual may come into contact with infected material. In some embodiments, the individual may be a neonate or newborn Some embodiments provide a method of ameliorating, preventing or treating an infection in an individual, the method comprising: filtering blood of the individual to separate $CD71^+$ cells from the blood. In some embodiments, the method further comprises identifying an individual with the infection. In some embodiments, the method further comprises identifying an individual at risk for infection.

Some embodiments provide a method of ameliorating, preventing or treating an infection in an individual, the method comprising administering to the individual an effective amount of an agent whereby the immunosuppressive effect of $CD71^+$ cells is inhibited. In some embodiments, the method further comprises identifying an individual with the infection. In some embodiments, the method further comprises identifying an individual at risk for infection.

Some embodiments provide a pharmaceutical composition for any one of the methods as disclosed and described herein for boosting an immune response in neonates and newborns comprising a $CD71^+$ inhibitor and a pharmaceutically acceptable carrier.

Some embodiments provide a pharmaceutical composition for boosting an immune response in neonates and newborns comprising a $CD71^+$ inhibitor and a pharmaceutically acceptable carrier.

In some embodiments of the methods and compositions disclosed and described herein, the anti-CD71 antibody may be a humanized antibody. In some embodiments of the methods and compositions disclosed and described herein, the anti-CD71 antibody may be a human antibody. In some embodiments of the methods and compositions disclosed and described herein, the anti-CD71 antibody may be R17217 monoclonal antibody. In some embodiments of the methods and compositions disclosed and described herein, the anti-CD71 antibody may be C2F2 monoclonal antibody.

Methods for making antibodies of all types, including fragments, are known in the art (See for example, Harlow and Lane, Antibodies: A Laboratory Manual, Cold Spring Harbor Laboratory, New York (1988)). Methods of immunization, including all necessary steps of preparing the immunogen in a suitable adjuvant, determining antibody binding, isolation of antibodies, methods for obtaining monoclonal antibodies, and humanization of monoclonal antibodies are all known to the skilled artisan The antibodies may be humanized antibodies or human antibodies. Antibodies can be humanized using a variety of techniques known in the art including CDR-grafting (EP 239,400: PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska et al., PNAS 91:969-973 (1994)), and chain shuffling (U.S. Pat. No. 5,565,332) the disclosures of which are incorporated herein by reference in their entireties.

The monoclonal antibodies as defined include antibodies derived from one species (such as murine, rabbit, goat, rat, human, etc.) as well as antibodies derived from two (or more) species, such as chimeric and humanized antibodies.

Completely human antibodies are particularly desirable for therapeutic treatment of human patients. Human antibodies can be made by a variety of methods known in the art including phage display methods using antibody libraries derived from human immunoglobulin sequences. See also U.S. Pat. Nos. 4,444,887 and 4,716,111; and PCT publications WO 98/46645, WO 98/50433, WO 98/24893, WO 98/16654, WO 96/34096, WO 96/33735, and WO 91/10741, each of which is incorporated herein by reference in its entirety.

Additional information regarding all types of antibodies, including humanized antibodies, human antibodies and antibody fragments can be found in WO 01/05998, which is incorporated herein by reference in its entirety.

Neutralizing antibodies can be prepared by the methods discussed above, possibly with an additional step of screening for neutralizing activity by, for example, a survival assay.

Methods Summary

Mice. C57BL/6 ($CD45.2^+$) and congenic CD45.1 mice were purchased from National Cancer Institute. Pregnant mice were checked twice daily for birth timing. All experiments were performed in accordance with institutional IACUC approved protocols.

Infection. Wild type Lm 10403s was grown in brain heart infusion media, back diluted to early log phase ($OD_{600}$ 0.1), resuspended in sterile saline, and inoculated intraperitoneally. For enumerating bacterial counts, serial dilutions of the liver and spleen homogenate were spread onto agar plates.

Cell transfer, purification, stimulation, and depletion. Splenocytes from adult CD45.1 mice ($5\times10^7$ cells) were injected intraperitoneally into 5 day old recipient $CD45.2^+$ mice. $CD71^+$ or immune lineage ($CD4^+$, $CD8^+$, $CD11b^+$, $CD11c^+$, $B220^+$, $NK1.1^+$) cells among neonatal splenocytes were purified by negative selection using biotin-conjugated antibodies and streptavidin linked magnetic beads. For stimulation and co-culture, splenocytes from adult CD45.1 mice ($5\times10^5$ cells) were cultured in 96 well round bottom plates individually or together with neonatal splenocytes at defined ratios, and stimulated with either heat killed Lm ($5\times10^6$/mL) or anti-CD3 antibody (0.25 μg/mL). For in vivo depletion, purified anti-Ter119 (Ter119), anti-CD71 (8D3), and rat IgG isotype control antibodies were administered intraperitoneally (100 μg per mouse) one day prior to infection.

Statistics. Differences in survival were compared using the Mantel-Cox logrank test. Differences in $\log_{10}$ CFUs, cytokine and cell activation levels between groups were analyzed using an unpaired Student's t test (Prism, Graph Pad) with $P<0.05$ taken as statistical significance.

Methods

Mice. Adult C57BL/6 ($CD45.2^+CD45.1^-$) and congenic CD45.1 ($CD45.2^-$) mice were purchased from National Cancer Institute. C57BL/6 mice were bred together, and pregnant mice were checked twice daily to establish birth timing. For infection or splenocyte cell harvest, 6, 9, 15 and 21 day old pups or 8 week old adult mice were utilized. All experiments were performed in accordance with institutional IACUC approved protocols.

Infection. The wild type *Listeria monocytogenes* (Lm) strain 10403s was grown in liquid brain heart infusion (BHI) media at 37° C., back diluted to early log phase ($OD_{600}$ 0.1), resuspended in sterile saline, and inoculated via an intraperitoneal (IP) route at a dose of $2\times10^2$ or $1\times10^3$ bacteria per mouse in 80 μL. The inoculum for each experiment was verified by spreading a diluted aliquot onto agar plates, and incubation overnight at 37° C. For enumerating bacterial counts, mice were euthanized 48 hours after infection, the liver and spleen dissected and homogenized in sterile saline containing 0.05% Triton X-100 to disperse intracellular bacteria, and serial dilutions of the organ homogenate spread onto agar plates as described[26].

Antibodies and flow cytometry. Fluorophore or biotin conjugated antibodies with specificity to mouse cell surface antigens and cytokines, and cell permeabilization reagents were purchased from eBioscience or BD Biosciences. Specifically, the following antibodies were used: anti-B220 (RA3-6B2), anti-CD4 (GK1.5), anti-CD8a (53-6.7), anti-CD11b (M1/70), anti-CD11c (N418), anti-CD25 (PC61.5), anti-CD69 (H1.2F3), anti-CD45.1 (A20), anti-CD45.2 (104), anti-CD71 (R17217 and C2F2), anti-NK1.1 (PK136), anti-Ter119 (TER-119), anti-IFN-γ (XMG1.2), anti-IL-12p40 (C17.8), and anti-TNF-α (MP6-XT22). Data acquisition was performed using a FACSCanto (BD Biosciences) cytometer, and analyzed with FlowJo (TreeStar) software. For in vivo depletion, purified anti-Ter119 (Ter119), anti-CD71 (8D3), and rat IgG isotype control antibodies were administered IP (100 μg per mouse) one day prior to infection.

Cell transfer and purification. Nucleated splenocytes were harvested into single cell suspensions by grinding between sterile frosted glass slides, incubation in Tris buffered ammonium chloride solution for red blood cell lysis, and filtering through nylon mesh. For adoptive transfer, $5\times10^7$ splenocytes from adult $CD45.1^+$ mice were injected IP into 5 day old recipient $CD45.2^+$ pups one day prior to infection. $CD71^+$ or immune lineage ($CD4^+$, $CD8^+$, $CD11b^+$, $CD11c^+$, $B220^+$, $NK1.1^+$) cells among neonatal splenocytes were purified by negative selection using biotin-conjugated antibodies and streptavidin linked magnetic beads (Miltenyi Biotec). The purity of cells after negative selection was verified to be ~95% for each experiment (FIG. 3B).

Co-Culture and stimulation. For ex vivo cytokine production, splenocytes were harvested 48 hours after infection, and cultured ($10^6$ cells/mL) in DMEM media supplemented with 10% fetal bovine serum and Brefeldin A (10 μg/mL). For co-culture assays, a fixed number ($5\times10^5$) of splenocytes from CD45.1 adult mice were cultured in 96 well round bottom plates individually or together with CD45.2 neonatal splenocyes at defined ratios, and stimulated for 5 hours with either heat killed Lm ($5\times10^6$/mL) or anti-CD3 Antibody (0.25 μg/mL). Heat killed Lm was prepared by growing Lm 10403s in BHI media to early log phase, washing and resuspension in sterile saline, and incubation at 70° C. for 30 minutes. Each batch was verified to be sterile by plating onto BHI agar plates, and then stored at −20° C. before use. For intracellular cytokine staining, the media was supplemented with Brefeldin A (10 μg/mL) during stimulation and coculture. For comparing cytokine production and cell activation between experiments, individual samples were normalized by plotting the percent maximal response compared with adult cells stimulated without neonatal cells in each experiment. For cytokine production in cell supernatants, a fixed concentration of CD45.1 adult splenocytes ($10^6$ cells/mL) were cultured individually or with an equal number of neonatal splenocytes, or neonatal splenocytes alone controls, were stimulated with heat killed Lm ($5\times10^6$/mL) for 72 hours, and thereafter the accumulated concentration of TNF-α and IL-6 measured by ELISA (R&D Systems).

Statistical analysis. Differences in survival between adult and neonatal mice after infection were compared using the Mantel-Cox logrank test. The distribution of $\log_{10}$ CFUs, cytokine and cell activation levels were first determined to be normally distributed, and thereafter, differences between groups were analyzed using an unpaired Student's t test (Prism, Graph Pad) with $P<0.05$ taken as statistical significance.

The following references are incorporated herein by reference in their entireties:

REFERENCES

1 PrabhuDas, M. et al. Challenges in infant immunity: implications for responses to infection and vaccines. Nature immunology 12, 189-194, (2011).

2 Kollmann, T. R., Levy, O., Montgomery, R. R. & Goriely, S. Innate immune function by Toll-like receptors: distinct responses in newborns and the elderly. Immunity 37, 771-783, (2012).

3 Zaghouani, H., Hoeman, C. M. & Adkins, B. Neonatal immunity: faulty T-helpers and the shortcomings of dendritic cells. Trends in immunology 30, 585-591, (2009).

4 Adkins, B., Leclerc, C. & Marshall-Clarke, S. Neonatal adaptive immunity comes of age. Nature reviews. Immunology 4, 553-564, (2004).

5 Fuchs, E. J., Ridge, J. P. & Matzinger, P. Response: immunological tolerance. Science 272, 1406-1408, (1996).

6 Ridge, J. P., Fuchs, E. J. & Matzinger, P. Neonatal tolerance revisited: turning on newborn T cells with dendritic cells. Science 271, 1723-1726 (1996).

7 Forsthuber, T., Yip, H. C. & Lehmann, P. V. Induction of TH1 and TH2 immunity in neonatal mice. Science 271, 1728-1730 (1996).

8 Kollmann, T. R. et al. Neonatal innate TLR-mediated responses are distinct from those of adults. J Immunol 183, 7150-7160, (2009).

9 Levy, O. et al. Selective impairment of TLR-mediated innate immunity in human newborns: neonatal blood plasma reduces monocyte TNF-alpha induction by bacterial lipopeptides, lipopolysaccharide, and imiquimod, but preserves the response to R-848. J Immunol 173, 4627-4634 (2004).

10 Lee, H. H. et al. Delayed maturation of an IL-12-producing dendritic cell subset explains the early Th2 bias in neonatal immunity. The Journal of Experimental Medicine 205, 2269-2280, (2008).

11 Adkins, B., Bu, Y., Cepero, E. & Perez, R. Exclusive Th2 primary effector function in spleens but mixed Th1/Th2 function in lymph nodes of murine neonates. J Immunol 164, 2347-2353 (2000).

12 Gellin, B. G. & Broome, C. V. Listeriosis. JAMA 261, 1313-1320 (1989).

13 Siegrist, C. A. Neonatal and early life vaccinology. Vaccine 19, 3331-3346 (2001).

14 Mold, J. E. & McCune, J. M. Immunological tolerance during fetal development: from mouse to man. Advances in Immunology 115, 73-111, (2012).

15 Havell, E. A. Evidence that tumor necrosis factor has an important role in antibacterial resistance. J Immunol 143, 2894-2899 (1989).

16 Harty, J. T. & Bevan, M. J. Specific immunity to *Listeria monocytogenes* in the absence of IFN gamma. Immunity 3, 109-117 (1995).

17 Pasparakis, M., Alexopoulou, L., Episkopou, V. & Kollias, G. Immune and inflammatory responses in TNF alpha-deficient mice: a critical requirement for TNF alpha in the formation of primary B cell follicles, follicular dendritic cell networks and germinal centers, and in the maturation of the humoral immune response. The Journal of Experimental Medicine 184, 1397-1411 (1996).

18 Brombacher, F. et al. IL-12 is dispensable for innate and adaptive immunity against low doses of *Listeria monocytogenes*. International Immunology 11, 325-332 (1999).

19 Trowbridge, I. S., Lesley, J. & Schulte, R. Murine cell surface transferrin receptor: studies with an anti-receptor monoclonal antibody. Journal of Cellular Physiology 112, 403-410, (1982).

20 Hermansen, M. C. Nucleated red blood cells in the fetus and newborn. Archives of disease in childhood. Fetal and neonatal edition 84, F211-215 (2001).

21 Marsee, D. K., Pinkus, G. S. & Yu, H. CD71 (transferrin receptor): an effective marker for erythroid precursors in bone marrow biopsy specimens. American Journal of Clinical Pathology 134, 429-435, (2010).

22 Dong, H. Y., Wilkes, S. & Yang, H. CD71 is selectively and ubiquitously expressed at high levels in erythroid precursors of all maturation stages: a comparative immunochemical study with glycophorin A and hemoglobin A. The American Journal of Surgical Pathology 35, 723-732, (2011).

23 Mold, J. E. et al. Maternal alloantigens promote the development of tolerogenic fetal regulatory T cells in utero. Science 322, 1562-1565, (2008).

24 Burlingham, W. J. & Benichou, G. Bidirectional alloreactivity: A proposed microchimerism-based solution to the NIMA paradox. Chimerism 3, 29-36, (2012).

25 Andrassy, J. et al. Tolerance to noninherited maternal MHC antigens in mice. J Immunol 171, 5554-5561 (2003).

26 Rowe, J. H., Ertelt, J. M., Aguilera, M. N., Farrar, M. A. & Way, S. S. Foxp3(+) regulatory T cell expansion required for sustaining pregnancy compromises host defense against prenatal bacterial pathogens. Cell Host & Microbe 10, 54-64, (2011).

27 Rowe, J. H., Ertelt, J. M., Xin, L. & Way, S. S. Pregnancy imprints regulatory memory that sustains anergy to fetal antigen. Nature 490, 102-106, (2012).

28 Aluvihare, V. R., Kallikourdis, M. & Betz, A. G. Regulatory T cells mediate maternal tolerance to the fetus. Nature Immunology 5, 266-271, (2004).

29 Samstein, R. M., Josefowicz, S. Z., Arvey, A., Treuting, P. M. & Rudensky, A. Y. Extrathymic generation of regulatory T cells in placental mammals mitigates maternal-fetal conflict. Cell 150, 29-38, (2012).

30 Leikin, S. L. et al. Mortality in children and adolescents with sickle cell disease. Cooperative Study of Sickle Cell Disease. Pediatrics 84, 500-508 (1989).

While this disclosure has been described in connection with what is presently considered to be practical exemplary embodiments, it is to be understood that the invention is not limited to the disclosed embodiments and is intended to cover various modifications and equivalent arrangements included within the spirit and scope of the appended claims.

What is claimed is:

1. A method of augmenting an immune response in a subject in need thereof, comprising:

a) identifying the subject; and b) administering to the subject an agent that specifically binds to CD71, wherein the agent that specifically binds to CD71 is an anti-CD71 antibody, wherein the subject is a neonate or a newborn, and wherein administration of the anti-CD71 antibody leads to an inhibition of an immune suppressive effect of $CD71^+$ cells.

2. The method of claim 1, wherein the anti-CD71 antibody is R17217.

3. The method of claim 1, wherein the anti-CD71 antibody is C2F2.

4. A method of treating or ameliorating an infection in a subject, comprising administering to the subject an agent that reduces the level of $CD71^+$ cells in the subject, wherein the agent specifically binds to CD71, wherein the agent is an anti-CD71 antibody, and wherein the subject is a neonate or a newborn.

5. The method of claim 4, wherein the anti-CD71 antibody is a humanized antibody.

6. The method of claim 4, wherein the anti-CD71 antibody is a human antibody.

7. The method of claim 4, wherein the agent downregulates the level of $CD71^+$ cells.

8. The method of claim 4, comprising identifying the subject at risk for the infection.

9. The method of claim 1, wherein the newborn is less than 28 days old.

10. The method of claim 4, wherein the newborn is less than 28 or days old.

* * * * *